(12) United States Patent
Hong et al.

(10) Patent No.: US 6,683,095 B2
(45) Date of Patent: Jan. 27, 2004

(54) CDK INHIBITORS HAVING 3-HYDROXYCHROMEN-4-ONE STRUCTURE

(75) Inventors: Chang-Yong Hong, Taejon (KR); Jin-Ho Lee, Taejon (KR); Tae-Sik Park, Taejon (KR); Jong-Hyun Kim, Taejon (KR); Sei-Hyun Choi, Taejon (KR); Sook-Kyung Yoon, Taejon (KR); Hyun-Ho Chung, Taejon (KR); Ho-Sun Son, Taejon (KR); Eunice Eun-Kyeong Kim, Taejon (KR); Seong-Gu Ro, Taejon (KR); Shin-Wu Jeong, Taejon (KR); Dong-Myung Kim, Taejon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 10/275,066

(22) PCT Filed: May 3, 2001

(86) PCT No.: PCT/KR01/00725

§ 371 (c)(1),
(2), (4) Date: Nov. 1, 2002

(87) PCT Pub. No.: WO01/83469

PCT Pub. Date: Nov. 8, 2001

(65) Prior Publication Data

US 2003/0125356 A1 Jul. 3, 2003

(30) Foreign Application Priority Data

May 3, 2000 (KR) ........................................ 2000/23705
Sep. 18, 2000 (KR) ........................................ 2000/54573
Sep. 18, 2000 (KR) ........................................ 2000/54577

(51) Int. Cl.$^7$ ..................... A61K 31/453; C07D 405/04
(52) U.S. Cl. .................... 514/320; 546/196; 546/283.1; 548/214; 514/337; 514/372
(58) Field of Search ................................ 514/320, 337, 514/372, 456; 546/196, 283.1; 548/214; 549/400

(56) References Cited

FOREIGN PATENT DOCUMENTS

| JP | 63-2925 A2 | 1/1988 |
|---|---|---|
| WO | WO 97/29779 A2 | 8/1997 |
| WO | WO 98/17662 A1 | 4/1998 |
| WO | WO 2000/12496 A1 | 3/2000 |

Primary Examiner—Charanjit S. Aulakh
(74) Attorney, Agent, or Firm—Birch, Stewart, Kolasch & Birch, LLP

(57) ABSTRACT

A novel 3-hydroxychromen-4-one derivative, pharmaceutically acceptable salt, hydrate, solvate or isomer thereof which is useful as an inhibitor for Cyclin Dependent Kinase ("CDK") is disclosed. Further, a process for preparing the compound and a composition for suppression or treatment of cancer and diseases induced by cell proliferation such as inflammation, angiostenosis, angiogenesis, etc. is disclosed comprising the compound as an active component together with pharmaceutically acceptable carriers.

5 Claims, No Drawings

CDK INHIBITORS HAVING 3-HYDROXYCHROMEN-4-ONE STRUCTURE

This application is the national phase under 35 U.S.C. §371 of PCT International Application No. PCT/KR01/00725 which has an International filing date of May 3, 2001, which designated the United States of America.

TECHNICAL FIELD

The present invention relates to a novel 3-hydroxychromen-4-one derivative represented by the following formula (1):

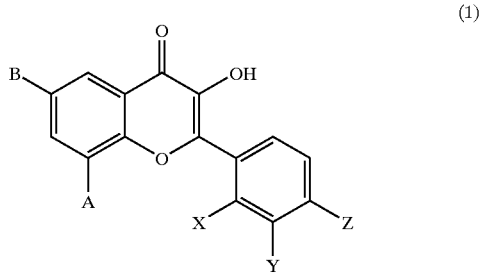

(1)

in which

A represents hydrogen or nitro, or represents amino which is optionally substituted by $C_1$–$C_4$-alkylcarbonyl or carbamoyl, or represents a structure selected from a group consisting of

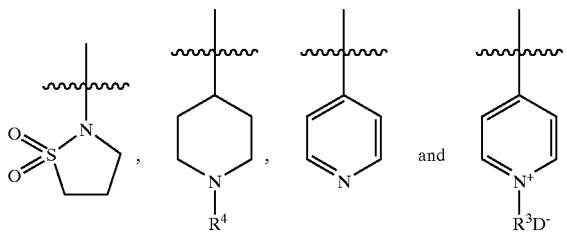

wherein $R^4$ represents hydrogen or $C_1$–$C_6$-alkyl which is optionally substituted by amino or hydroxy, $R^3$ represents $C_1$–$C_6$-alkyl which is optionally substituted by amino or hydroxy, and D represents halogen, B represents methyl, or represents amino which is optionally mono- or disubstituted by substituents selected from a group consisting of $C_1$–$C_6$-alkyl, hydroxy-$C_1$–$C_6$-alkyl, $C_3$–$C_6$-cycloalkyl, acetyl, phenyl, benzyl and piperidinyl, X, Y and Z independently of one another represent hydrogen, hydroxy, nitro, cyano or halogen, or represent amino which is optionally substituted by $C_1$–$C_4$-alkyl, $C_1$–$C_4$-alkylcarbonyl or carbamoyl, or represent $C_1$–$C_4$-alkyl which is optionally substituted by hydroxy or halogen, pharmaceutically acceptable salt, hydrate, solvate or isomer thereof which is useful as an inhibitor for Cyclin Dependent Kinase (hereinafter, referred to as "CDK").

The present invention further relates to a process for preparing the compound of formula (1) and to a composition for suppression or treatment of cancer and diseases induced by cell proliferation such as inflammation, angiostenosis, angiogenesis, etc. which comprises the compound of formula (1) as an active component together with pharmaceutically acceptable carriers.

BACKGROUND ART

Researches on cell division process in molecular level have been extensively performed from the late 1980's through study of division of frog oocytes, analysis several yeast cell growth or characterization of induced mutants by radiation and study of the tumor suppressor Rb. In the 1990's, it was discovered that cell growth regulators of small size control the cell division process (i.e. growth, differentiation, cytogenesis, aging and apoptosis, etc.) through their own regulatory function. These results were very useful for more precise understanding of the pathology of several diseases. A representative example is cancer. In transformation process from normal cells to cancer cells, it was frequently observed that cell growth regulators lose their own function. That is, in cancer cells, the cell growth regulators show an abnormal activity, which is intimately associated with invasion/metastasis, the most crucial factor considered in the cancerpathology. Particularly, cell cycle deregulation is recognized to be a direct cause of cancer since cancer occurs when overexpression or knock-out of cell growth regulators is induced in the transformed animals.

The cell growth is under positive or negative regulation in the same manner as other biological regulations. The major pathway of cell cycle regulation known up to now is based on CDK activity and as a result of studies on many cancer cells and carcinogenesis mechanisms, it was confirmed that problems of positive or negative regulation on CDK activity result in carcinogenesis in many cases. That is, cancer may occur when well-balanced regulation or timely regulation is upset.

The representative CDKs of mammals are CDK4(cyclin dependent kinase 4) which shows its activity in mid-G1 phase of cell cycle, CDK2 which shows its activity in mid-G1 and S phases, CDC2(CDK1) which shows its activity in G2-M phase. It has been known that CDK4 and CDK2 activities are regulated by check point of G1-S cell cycle and CDC2 activity by check point of G2-M. In many cancer cells, abnormalities appear in the regulatory mechanism of CDK4, CDK2 and CDC2(CDK1) and in fact, it was confirmed that artificially induced abnormalities cause cancer in the transformed animals. Therefore, the typical cyclin dependent kinases, i.e., CDK4, CDK2 and CDC2(CDK1) are suitable as a target of anti-cancer agents. Those kinases also become a target in developing an agent for suppression or treatment of cancer and diseases induced by cell proliferation such as inflammation, angiostenosis, angiogenesis, etc.

The results of studies on the relation between these CDKs and carcinogenesis will be explained in more detail in the following.

The relation between the abnormal regulation of CDK4 activity and carcinogenesis is observed in several cancer tissues. Deletion of p16 and p15 genes producing the proteins that inhibit CDK4 activity or overexpression of cyclin D1 that is essential for the CDK4 activity is observed in several kinds of cancer, which suggests that malignant phenotype may be induced when CDK4 activity is deregulated. Furthermore, it was reported that p16 knocked-out mouse has such a high carcinogenesis rate as p53 knocked-out mouse, which suggests that malfunction of p16 on CDK4 regulation is a cause of carcinogenesis. From these experimental results, deregulation of CDK4 activity may be a certain cause of carcinogenesis and play a role in maintenance of phenotype of cancer cell. Therefore, it is highly probable that CDK4 inhibitors have an anti-cancer effect.

It was reported that overexpression of cyclin E that is essential for CDK2 activity is observed in some breast cancers, is deeply associated with metastasis of breast cancer, inhibits cell apoptosis under low serum condition, and induces anchorage independent growth, and that hyperproliferation and neoplasia of mammary epithelial cells are observed in transformed animal where CDK2 is overexpressed using MMTV promoter. This strongly suggests that CDK2 activity is related with the progress or maintenance of cell transformation and CDK2 inhibitors may have an anticancer effect.

Furthermore, it has been gradually discovered that CDC2 (CDK1), CDK3, CDK5, CDK6, CDK7, etc. play an important role in each phase of cell division. These are classified into CDKs family. In addition to cyclin D1 and E, cyclin A, B, C, D2, D3, D4, F and G are also classified into the same family.

On the basis of the above-mentioned researches, efficient inhibitors against these CDKs are recognized to be useful as an anti-cancer agent. Therefore, recently, some inhibitors have been developed.

As the effective CDKs inhibitor developed hitherto, Flavopiridol (EP 0,241,003 (1987) and 0,366,061 (1990)) represented by the following formula (2) can be mentioned:

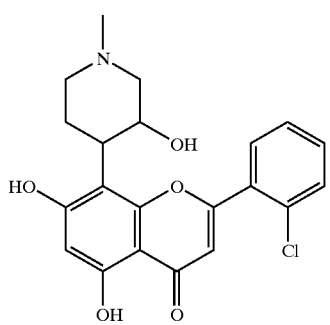

(2)

In addition, a purine derivative represented by the following formula (3):

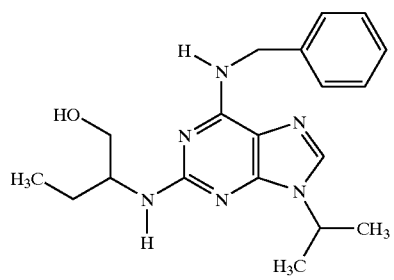

(3)

has been reported (WO 97/20842), and a compound represented by the following formula (4):

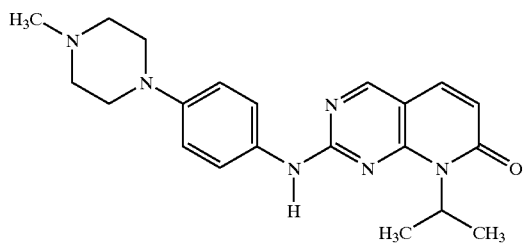

(4)

having a quite different structure has been reported as an effective CDKs inhibitor (WO 98/33798).

DISCLOSURE OF INVENTION

However, the CDKs inhibitors developed up to now did not show satisfactory effects. Therefore, the present inventors have made extensive researches on CDKs inhibitors, particularly on flavone compounds and as a result, found that the above compound of formula (1) which has a quite different structure effectively inhibits the aforementioned CDKs and then, completed the present invention.

Therefore, the object of the present invention is to provide a novel 3-hydroxychromen-4-one derivative of formula (1), as defined above, pharmaceutically acceptable salt, hydrate, solvate or isomer thereof having an inhibitory activity for CDKs.

It is another object of the present invention to provide a process for preparing the compound of formula (1).

It is still another object of the present invention to provide a composition for suppression or treatment of cancer and diseases induced by cell proliferation such as inflammation, angiostenosis, angiogenesis, etc. comprising the compound of formula (1) as an active component together with pharmaceutically acceptable carriers.

In this specification, CDKs includes CDK2, CDK4, CDC2(CDK1), CDK3, CDK5, CDK6, CDK7, etc. and cyclins include cyclin D1, E, A, B, C, D2, D3, D4, F and G.

BEST MODE FOR CARRYING OUT THE INVENTION

The present invention relates to a novel 3-hydroxychromen-4-one derivative represented by the following formula (1):

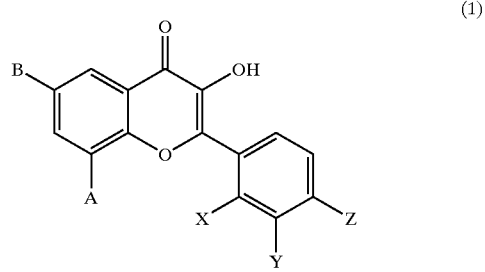

(1)

in which

A represents hydrogen or nitro, or represents amino which is optionally substituted by $C_1$–$C_4$-alkylcarbonyl or carbamoyl, or represents a structure selected from a group consisting of

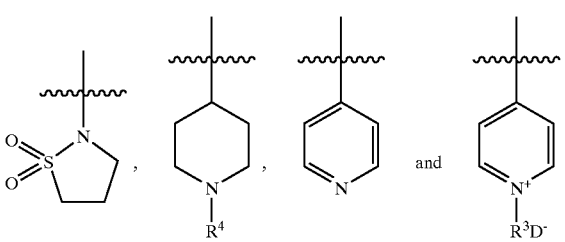

wherein $R^4$ represents hydrogen or $C_1$–$C_6$-alkyl which is optionally substituted by amino or hydroxy, $R^3$ represents $C_1$–$C_6$-alkyl which is optionally substituted by amino or hydroxy and D represents halogen, B represents methyl, or represents amino which is optionally mono- or disubstituted by substituents selected from a group consisting of $C_1$–$C_6$-alkyl, hydroxy-$C_1$–$C_6$-alkyl, $C_3$–$C_6$-cycloalkyl, acetyl, phenyl, benzyl and piperidinyl, X, Y and Z independently of one another represent hydrogen, hydroxy, nitro, cyano or halogen, or represent amino which is optionally substituted by $C_1$–$C_4$-alkyl, $C_1$–$C_4$-alkylcarbonyl or carbamoyl, or represent $C_1$–$C_4$-alkyl which is optionally substituted by hydroxy or halogen, pharmaceutically acceptable salt, hydrate, solvate or isomer thereof which exhibits a suppressive and therapeutic effect for cancer and diseases induced by cell proliferation such as inflammation, angiostenosis, angiogenesis, etc. by the inhibition of CDKs activities.

Since the compound of formula (1) according to the present invention may have asymmetric carbon atoms depending on the substituents, they can be present in the form of individual enantiomers or diastereomers, or mixtures thereof including racemates. Thus, the present invention also includes all of these isomers and their mixtures.

Also, the compound of formula (1) according to the present invention can form a pharmaceutically acceptable salt. Such salt includes non-toxic acid addition salt containing pharmaceutically acceptable anion, for example a salt with inorganic acids such as hydrochloric acid, sulfuric acid, nitric acid, phosphoric acid, hydrobromic acid, hydriodic acid, etc., a salt with organic carboxylic acids such as tartaric acid, formic acid, citric acid, acetic acid, trichloroacetic acid, trofluoroacetic acid, gluconic acid, benzoic acid, lactic acid, fumaric acid, maleic acid, etc., or a salt with sulfonic acids such as methanesulfonic acid, benzenesulfonic acid, p-toluenesulfonic acid, naphthalenesulfonic acid, etc.

Typical examples of the compound of formula (1) according to the present invention are 8-amino-2-(3-amino-4-hydroxyphenyl)-3-hydroxy-6-methyl-4H-chromen-4-one (Compound 1);

2-(4-hydroxy-3-nitrophenyl)-3-hydroxy-6-methyl-8-nitro-4H-chromen-4-one (Compound 2);

N-[2-(4-hydroxy-3-nitrophenyl)-3-hydroxy-6-methyl-4-oxo-4H-chromen-8-yl]acetamide (Compound 3);

8-amino-2-(4-hydroxyphenyl)-3-hydroxy-6-methyl-4H-chromen-4-one (Compound 4);

2-(3-amino-4-hydroxyphenyl)-3-hydroxy-6-methyl-4H-chromen-4-one (Compound 5);

N-[2-hydroxy-5-(3-hydroxy-6-methyl-4-oxo-4H-chromen-2-yl)phenyl]acetamide (Compound 6);

N-{2-[4-hydroxy-3-(isopropylamino)phenyl]-3-hydroxy-6-methyl-4-oxo-4H-chromen-8-yl}acetamide (Compound 7A);

N-[2-(3-amino-4-hydroxyphenyl)-3-hydroxy-6-methyl-4-oxo-4H-chromen-8-yl]acetamide (Compound 7B);

2-(3-fluoro-4-hydroxyphenyl)-3-hydroxy-6-methyl-8-nitro-4H-chromen-4-one (Compound 8);

8-amino-2-(3-fluoro-4-hydroxyphenyl)-3-hydroxy-6-methyl-4H-chromen-4-one (Compound 9);

N-{5-[8-(ureido)-3-hydroxy-6-methyl-4-oxo-4H-chromen-2-yl]-2-hydroxyphenyl}urea (Compound 10);

8-amino-2-(4-aminophenyl)-3-hydroxy-6-methyl-4H-chromen-4-one (Compound 11);

8-amino-3-hydroxy-2-(3-hydroxyphenyl)-6-methyl-4H-chromen-4-one (Compound 12);

3-hydroxy-6-methyl-2-(2,3,4-trihydroxyphenyl)-4H-chromen-4-one (Compound 13);

2-(2-bromo-3,4-dihydroxyphenyl)-3-hydroxy-6-methyl-4H-chromen-4-one (Compound 14);

2-[3-hydroxy-2-(4-hydroxyphenyl)-6-methyl-4-oxo-4H-chromen-8-yl]-1$\lambda^6$-isothiazolidin-1,1-dione (Compound 15);

2-[2-(3-fluoro-4-hydroxyphenyl)-3-hydroxy-6-methyl-4-oxo-4H-chromen-8-yl]-1$\lambda^6$-isothiazolidin-1,1-dione (Compound 16);

2-[2-(3-chloro-4-hydroxyphenyl)-3-hydroxy-6-methyl-4-oxo-4H-chromen-8-yl]-1$\lambda^6$-isothiazolidin-1,1-dione (Compound 17);

2-[2-(3-bromo-4-hydroxyphenyl)-3-hydroxy-6-methyl-4-oxo-4H-chromen-8-yl]-1$\lambda^6$-isothiazolidin-1,1-dione (Compound 18);

5-[8-(1,1-dioxo-1$\lambda^6$-isothiazolidin-2-yl)-3-hydroxy-6-methyl-4-oxo-4H-chromen-2-yl]-2-hydroxybenzonitrile (Compound 19);

2-[2-(2,4-dihydroxyphenyl)-3-hydroxy-6-methyl-4-oxo-4H-chromen-8-yl]-1$\lambda^6$-isothiazolidin-1,1-dione (Compound 20);

2-[2-(3-chloro-4-fluorophenyl)-3-hydroxy-6-methyl-4-oxo-4H-chromen-8-yl]-1$\lambda^6$-isothiazolidin-1,1-dione (Compound 21);

2-[3-hydroxy-2-(4-hydroxy-3-methylphenyl)-6-methyl-4-oxo-4H-chromen-8-yl]-1$\lambda^6$-isothiazolidin-1,1-dione (Compound 22);

2-{3-hydroxy-2-[4-hydroxy-3-(hydroxymethyl)phenyl]-6-methyl-4-oxo-4H-chromen-8-yl}-1$\lambda^6$-isothiazolidin-1,1-dione (Compound 23);

2-[3-hydroxy-2-(4-hydroxy-3-trifluoromethylphenyl)-6-methyl-4-oxo-4H-chromen-8-yl]-1$\lambda^6$-isothiazolidin-1,1-dione (Compound 24);

2-[6-amino-3-hydroxy-2-(4-hydroxyphenyl)-4-oxo-4H-chromen-8-yl]-1$\lambda^6$-isothiazolidin-1,1-dione (Compound 25);

2-[6-(dimethylamino)-3-hydroxy-2-(4-hydroxyphenyl)-4-oxo-4H-chromen-8-y]-1$\lambda^6$-isothiazolidin-1,1-dione (Compound 26);

2-[6-(diethylamino)-3-hydroxy-2-(4-hydroxyphenyl)-4-oxo-4H-chromen-8-yl]-1$\lambda^6$-isothiazolidin-1,1-dione (Compound 27);

2-[6-(benzylamino)-3-hydroxy-2-(4-hydroxyphenyl)-4-oxo-4H-chromen-8-yl]-1$\lambda^6$-isothiazolidin-1,1-dione (Compound 28);

2-[3-hydroxy-2-(4-hydroxyphenyl)-4-oxo-6-(4-piperidinylamino)-4H-chromen-8-yl]-1$\lambda^6$-isothiazolidin-1,1-dione (Compound 29);

2-[6-(cyclohexylamino)-3-hydroxy-2-(4-hydroxyphenyl)-4-oxo-4H-chromen-8-yl]-1$\lambda^6$-isothiazolidin-1,1-dione (Compound 30);

2-[6-anilino-3-hydroxy-2-(4-hydroxyphenyl)-4-oxo-4H-chromen-8-yl]-1$\lambda^6$-isothiazolidin-1,1-dione (Compound 31);

2-[3-hydroxy-2-(4-hydroxyphenyl)-6-(methylamino)-4-oxo-4H-chromen-8-yl]-1$\lambda^6$-isothiazolidin-1,1-dione (Compound 32);

2-{3-hydroxy-6-[(2-hydroxyethyl)(methyl)amino]-2-(4-hydroxyphenyl)-4-oxo-4H-chromen-8-yl}-1$\lambda^6$-isothiazolidin-1,1-dione (Compound 33);

N-[2-(3-chloro-4-hydroxyphenyl)-8-(1,1dioxo-1$\lambda^6$-isothiazolidin-2-yl)-3-hydroxy-4-oxo-4H-chromen-6-yl]acetamide (Compound 34);

2-[6-amino-2-(3-chloro-4-hydroxyphenyl)-3-hydroxy-4-oxo-4H-chromen-8-yl]-1$\lambda^6$-isothiazolidin-1,1-dione (Compound 35);

2-[2-(3-chloro-4-hydroxyphenyl)-6-(dimethylamino)-3-hydroxy-4-oxo-4H-chromen-8-yl]-1$\lambda^6$-isothiazolidin-1,1-dione (Compound 36);

2-[2-(3-chloro-4-hydroxyphenyl)-6-(methylamino)-3-hydroxy-4-oxo-4H-chromen-8-yl]-1$\lambda^6$-isothiazolidin-1,1-dione (Compound 37);

2-(3-chloro-4-hydroxyphenyl)-3-hydroxy-6-methyl-8-(1-methyl-4-piperidinyl)-4H-chromen-4-one (Compound 38);

2-(3-chloro-4-hydroxyphenyl)-3-hydroxy-6-methyl-8-(4-pyridinyl)-4H-chromen-4-one (Compound 39);

4-[2-(3-chloro-4-hydroxyphenyl)-3-hydroxy-6-methyl-4-oxo-4H-chromen-8-yl]-1-methylpyridinium bromide (Compound 40);

2-(4-hydroxyphenyl)-3-hydroxy-6-methyl-8-(1-methyl-4-piperidinyl)-4H-chromen-4-one (Compound 41);

3-hydroxy-2-(4-hydroxy-3-methylphenyl)-6-methyl-8-(1-methyl-4-piperidinyl)-4H-chromen-4-one (Compound 42);

3-hydroxy-2-(4-hydroxy-3-trifluoromethylphenyl)-6-methyl-8-(1-methyl-4-piperidinyl)-4H-chromen-4-one (Compound 43);

2-(3-chloro-4-hydroxyphenyl)-3-hydroxy-8-[1-(2-hydroxyethyl)-4-piperidinyl]-6-methyl-4H-chromen-4-one (Compound 44); and 8-[1-(2-aminoethyl)-4-piperidinyl]-2-(3-chloro-4-hydroxyphenyl)-3-hydroxy-6-methyl-4H-chromen-4-one (Compound 45).

The compound of formula (1) of the present invention may be prepared by a process as described in the following and thus, it is another object of the present invention to provide such a process.

The compound of formula (1) of the present invention may be prepared characterized in that (a) a compound represented by the following formula (5):

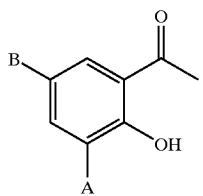

(5)

in which A and B are defined as previously described, is reacted with an aldehyde represented by the following formula (6):

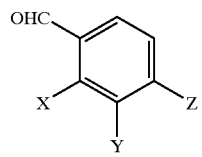

(6)

in which X, Y and Z are defined as previously described, to produce a compound represented by the following formula (7):

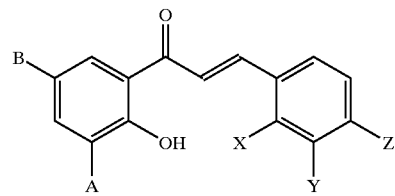

(7)

in which A, B, X, Y and Z are defined as previously described, and the compound of formula (7) thus prepared is cyclized in the presence of a base to produce the compound of formula (1);

(b) a compound represented by the following formula (8):

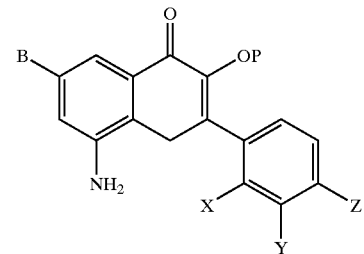

(8)

in which B, X, Y and Z are defined as previously described and P represents hydroxy-protecting group, preferably methyl or benzyl, is reacted with 3-chloropropanesulfonyl-chloride in the presence of a base and a catalyst to produce a compound represented by the following formula (9):

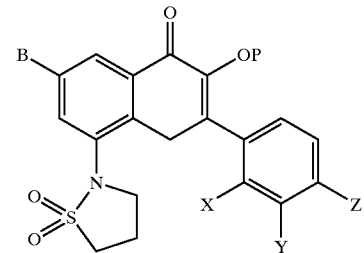

(9)

in which B, X, Y, Z and P are defined as previously described, and the compound of formula (9) thus prepared is deprotected to produce a compound represented by the following formula (1a):

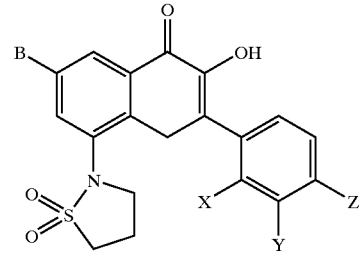

(Ia)

in which B, X, Y and Z are defined as previously described;

(c) a compound represented by the following formula (10):

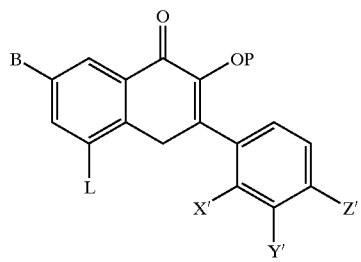
(10)

in which B and P are defined as previously described, L represents leaving group, preferably halogen, and X', Y' and Z' each are identical with X, Y and Z, respectively, but hydroxy group(s) is(are) protected, is reacted with 4-halogenopyridine in the presence of a base and a catalyst and then deprotected to produce a compound represented by the following formula (1b):

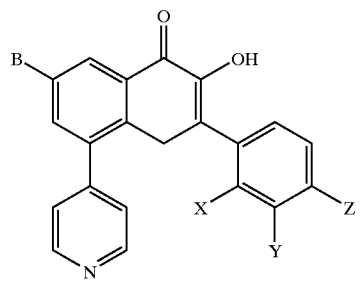
(Ib)

in which B, X, Y and Z are defined as previously described;

(d) the compound obtained before the deprotection step in process variant (c) is reacted with a compound represented by the following formula (11):

$R^3D$                  (11).

in which $R^3$ and D are defined as previously described, and then deprotected to produce a compound represented by the following formula (1c):

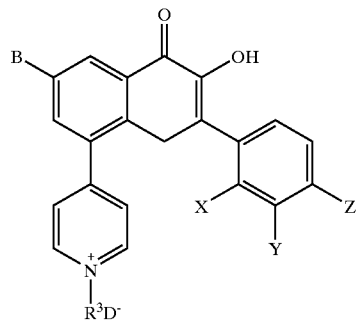
(Ic)

in which B, X, Y, Z, $R^3$ and D are defined as previously described;

(e) the compound obtained before the deprotection step in process variant (d) is reduced and deprotected to produce a compound represented by the following formula (1d):

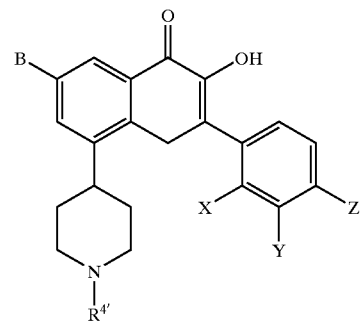
(Id)

in which B, X, Y and Z are defined as previously described and $R^{4'}$ is identical with $R^4$ but other than hydrogen;

or further hydrolysis protection, deprotection, reduction or amidation reaction may be carried out.

Hereinafter, the process according to the present invention is more specifically explained.

In process variant (a), the 2-hydroxyacetophenone derivative of formula (5) is reacted with 3 equivalents of the benzaldehyde derivative of formula (6) based on the compound of formula (5) to produce the compound of formula (7). As the base, 3 equivalents of sodium hydroxide based on the compound of formula (5) are preferably used. The reaction is preferably carried out in 80% aqueous ethanol solution for 3 hours at room temperature. Subsequently, the compound of formula (7) thus obtained is reacted in methanol solvent in the presence of excess 10% aqueous sodium hydroxide solution and excess hydrogen peroxide for 2 hours at room temperature to produce the compound of formula (1).

In process variant (b), the compound of formula (8) is dissolved in a solvent such as dichloromethane, reacted with 3-chloropropanesulfonylchloride in the presence of triethylamine and catalytic amount of dimethylaminopyridine at room temperature, and then concentrated. The resulting residue is dissolved again in dimethylformamide solvent and aqueous sodium hydroxide solution is added thereto. The mixture thus obtained is reacted for 30 minutes at 50° C. to produce the compound of formula (9). The compound of formula (9) is then reduced with hydrogen gas under a solvent system such as methanol/dichloromethane, or reacted with borontribromide in a solvent such as dichloromethane to produce the compound of formula (1a).

The compound of formula (8) used as a starting material in process variant (b) may be prepared according to the method as depicted in the following reaction scheme 1:

Reaction Scheme 1

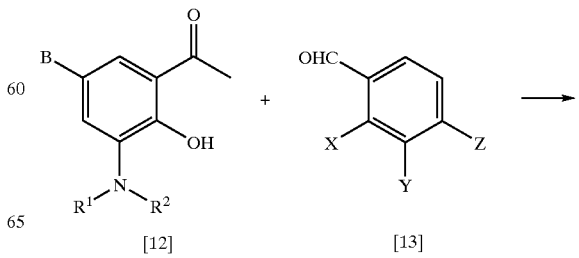

-continued

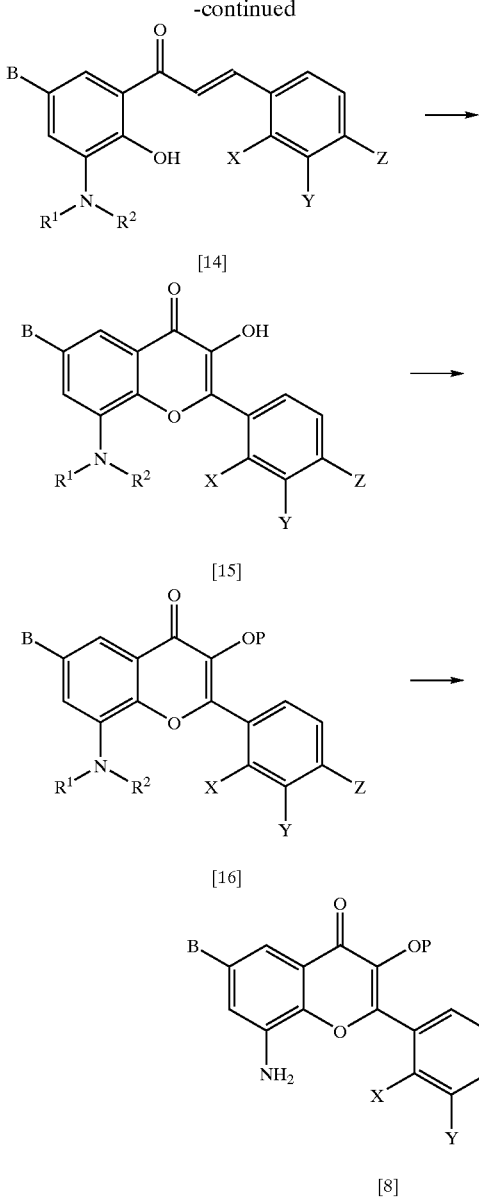

in which
B, X, Y, Z and P are defined as previously described, and R$^1$ and R$^2$ independently of one another represent hydrogen, oxo or acyl group, but both of them are not hydrogen.

In the reaction scheme 1, the process for preparing the compound of formula (15) from the compound of formula (12) may be carried out according to the same procedure as process variant (a). The compound of formula (15) thus prepared is refluxed with iodomethane or benzyl bromide in acetone solvent in the presence of potassium carbonate to produce the compound of formula (16) wherein 3-hydroxy group on the chromene ring is protected by a group of methyl or benzyl. The compound of formula (16) wherein 8-position of the chromene ring is substituted by nitro group is reduced by hydrogen gas. Otherwise, when the same position in the compound of formula (16) is substituted by acylamino group, BOC group is introduced into the amide group and the resulting compound is hydrolyzed to produce the compound of formula (8).

Process variants (c), (d) and (e) may be explained as follows. The starting compound of formula (10) is heated with 1.5 equivalent of bispinacolatodiboron, 3 equivalents of potassium acetate and 5 mol % of dichlorobistriphenylphosphine palladium in N,N-dimethylformamide solvent under nitrogen atmosphere to 80 to 90° C. and reacted for 2 hours. The reactants are cooled to room temperature, reacted with 2 equivalents of 4-bromopyridine hydrochloride, 5 mol % of dichlorobistriphenylphosphine palladium and 5 equivalents of 2M aqueous sodium carbonate solution for 15 hours, and then deprotected to produce the compound of formula (1b). The compound obtained before deprotection step to the formula (1b) is heated under reflux with 2 equivalents of the compound of formula (11) in acetone or acetonitrile solvent for 3 hours and then deprotected to produce the compound of formula (1c). Also, the compound obtained before deprotection step to the formula (1c) is dissolved in 50% methanol/dichloromethane, reacted with 5 mol % of platinum oxide under room temperature and 1 atm of hydrogen atmosphere for 48 hours, and then deprotected to produce the compound of formula (1d). In process variants (c), (d) and (e), the deprotection step is carried out by adding the compound to dry dichloromethane, adding 5 equivalents of borontribromide thereto, and reacting for 10 hours at room temperature.

Further, the compound of formula (10) used as a starting material in process variants (c), (d) and (e) may be prepared according to the method as depicted in the following reaction scheme 2:

Reaction Scheme 2

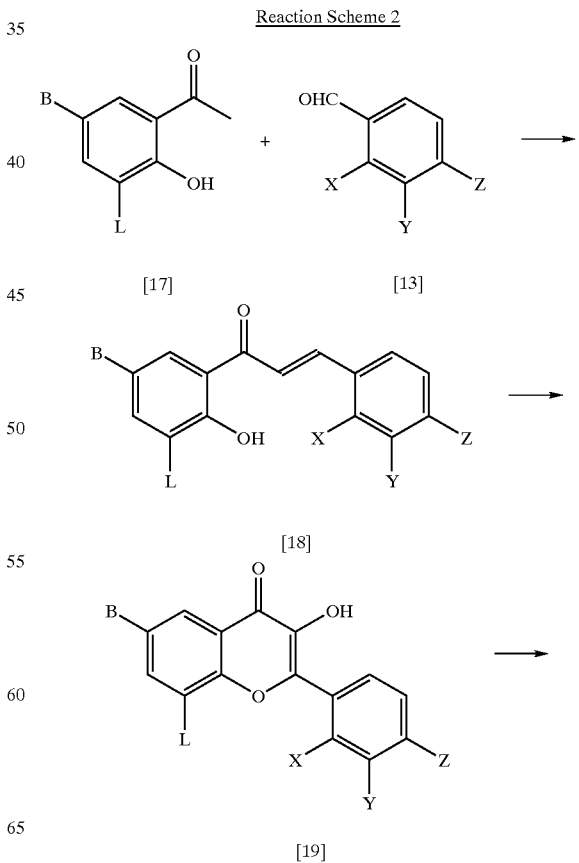

-continued

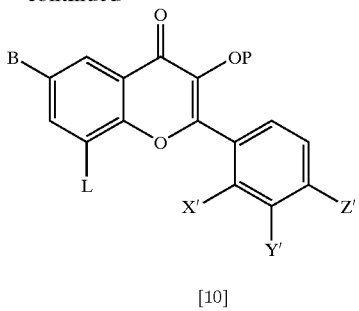

[10]

in which

B, L, X Y, Z, P, X', Y' and Z' are defined as previously described.

In reaction scheme 2, the compound of formula (17) is reacted with the benzaldehyde of formula (13) and 3 equivalents of sodium hydroxide in the solvent of 80% aqueous ethanol solution for 17 hours at room temperature to produce the compound of formula (18). This compound is reacted with 3 equivalents of 10% aqueous sodium hydroxide solution and 3 equivalents of hydrogen peroxide in methanol solvent for 3 hours at room temperature to produce the compound of formula (19). The compound of formula (19) thus obtained is reacted with 2 equivalents of iodomethane and potassium carbonate in acetone solvent for 30 minutes at room temperature to produce the compound of formula (10).

The reaction conditions including reaction solvent, base, amount of reactants, etc. in the process according to the present invention are not restricted to those as mentioned above and can easily be selected by optionally combining the various synthetic ways described in the present specification or known in the art. And such a combination may be easily carried out by one of ordinary skill in the art. The following preparations and examples may also be referred to the specific reaction conditions of the above process.

After the reaction is completed, the product may be isolated and purified by conventional work up processes such as chromatography, recrystallization, etc.

The compound of formula (1) of the present invention can be effectively used as medicines for suppression or treatment of cancer and diseases induced by cell proliferation such as inflammation, angiostenosis, angiogenesis, etc. due to its excellent inhibitory activity against CDKs. Therefore, another object of the present invention is to provide a composition for suppression or treatment of cancer and diseases induced by cell proliferation such as inflammation, angiostenosis, angiogenesis, etc. characterized by comprising the compound of formula (1), pharmaceutically acceptable salt, hydrate, solvate or isomer thereof as an active component together with pharmaceutically acceptable carriers.

When the active compound according to the present invention is used for clinical purpose, it is preferably administered to the subject patient in an amount ranging from 1 to 50 mg per kg of body weight a day. The total daily dosage may be administered in one time or over several times. However, the specific administration dosage for the specific patient can be varied with the specific compound used, body weight of the subject patient, sex, hygienic condition, diet, time or method of administration, excretion rate, mixing ratio of the agent, severity of the disease to be treated, etc.

The compound of the present invention may be administered in the form of injections or oral preparations.

Injections, for example, sterilized aqueous or oily suspension for injection, can be prepared according to the known procedure using suitable dispersing agent, wetting agent, or suspending agent. Solvents that can be used for preparing injections include water, Ringer's fluid and isotonic NaCl solution, and also sterilized fixing oil may be conveniently used as the solvent or suspending media. Any non-stimulative fixing oil including mono-, di-glyceride may be used for this purpose. Fatty acid such as oleic acid may also be used for injections.

As the solid preparation for oral administration, capsules, tablets, pills, powders and granules, etc., preferably capsules and tablets can be mentioned. It is also desirable for tablets and pills to be formulated into enteric-coated preparation. The solid preparations may be prepared by mixing the active compound of formula (1) according to the present invention with at least one carrier selected from a group consisting of inactive diluents such as sucrose, lactose, starch, etc., lubricants such as magnesium stearate, disintegrating agent and binding agent.

When the compound of the present invention is clinically administered for the purpose of treating cancer, the active compound of formula (1) may be simultaneously administered with one or more selected from the known anti-cancer agents. As the anti-cancer agent that can be administered together with the compound of the present invention, 5-fluorouracil, cisplatin, doxorubicin, taxol, Gemcitabine, etc. can be mentioned.

However, anti-cancer preparations containing the compound of the present invention are not limited to those as explained above, and any agent capable of preventing or treating cancer may be included.

The present invention will be more specifically explained in the following examples and experiments. However, it should be understand that these examples and experiments are intended to illustrate the present invention but not in any manner to limit the scope of the present invention.

Preparation 1

Synthesis of (E)-3-[4-(benzyloxy)-3-nitrophenyl]-1-(2-hydroxy-5-methyl-3-nitrophenyl)-2-propen-1-one 2-hydroxy-5-methyl-3-nitroacetophenone (200 mg, 1.02 mmol), 4-benzyloxy-3-nitrobenzaldehyde (300 mg, 1.16 mmol) and 3 equivalents of sodium hydroxide (120 mg) were introduced into 80% aqueous ethanol solution and the resulting mixture was stirred for 3 hours at room temperature. The reaction solution was acidified by 2N hydrochloric acid solution and diluted with water. The resulting solid was filtered, washed with large amount of water and methanol, and then dried to give 430 mg (Yield 97%) of the title compound as a yellow solid.

$^1$H NMR (CDCl$_3$, ppm); δ8.06–7.75 (5H, m), 7.60–7.15 (7H, m), 5.31 (2H, s), 2.43 (3H, s)

FAB MS(m/e)=435[M$^+$+1]

Preparation 2

Synthesis of 2-[4-(benzyloxy)-3-nitrophenyl]-3-hydroxy-6-methyl-8-nitro-4H-chromen-4-one The compound prepared in Preparation 1 (400 mg, 0.92 mmol) was introduced into methanol, and aqueous hydrogen peroxide (0.5 ml) and 10% aqueous sodium hydroxide solution (0.5 ml) were added thereto at room temperature. The resulting mixture was stirred for 2 hours at room temperature, acidified by 2N hydrochloric acid solution, and diluted with water. The solid having a pale yellow color thus obtained was filtered, washed with large amount of water and methanol, and then dried to give 200 mg (Yield 48.5%) of the title compound.

$^1$H NMR (CDCl$_3$, ppm); δ8.84 (2H, s), 8.44 (1H, s), 8.19 (2H, d), 7.34–7.17 (5H, m)

FAB MS(m/e)=449[M$^+$+1]

EXAMPLE 1
Synthesis of 8-amino-2-(3-amino-4-hydroxyphenyl)-3-hydroxy-6-methyl-4H-chromen-4-one (Compound 1)

The compound prepared in Preparation 2 (100 mg, 0.22 mmol) was dissolved in 10% methanol/dichloromethane solvent and catalytic amount of 10% Pd/C was added. The resulting mixture was reacted under hydrogen pressure of 50 psi for 2 hours, filtered through a cellite pad, and concentrated to give 60 mg (Yield 90%) of the title compound.

$^1$H NMR (DMSO-$d_6$, ppm); δ8.92 (1H, s), 7.66 (1H, s), 7.56 (1H, d), 7.03 (1H, s), 6.81 (2H, m), 5.51 (2H, s), 2.32 (3H, s)

FAB MS (m/e)=299[M$^+$+1]

EXAMPLE 2
Synthesis of 2-(4-hydroxy-3-nitrophenyl)-3-hydroxy-6methyl-8-nitro-4H-chromen-4-one (Compound 2)

The compound prepared in Preparation 2 (20 mg, 44.6 μmol) was dissolved in dichloromethane (2 ml), excessive amount of borontribromide was added, and the resulting mixture was reacted for 2 hours at room temperature. The remaining borontribromide was decomposed with methanol and then concentrated under reduced pressure. The solid thus obtained was washed with dichloromethane to give 15.6 mg (Yield 98%) of the title compound.

$^1$H NMR (CDCl$_3$, ppm); δ10.86 (1H, s), 9.26 (1H, s), 8.60 (1H, s), 8.35 (2H, d), 7.36 (1H, m), 7.10 (1H, s)

FAB MS (m/e)=359[M$^+$+1]

Preparation 3
Synthesis of N-(3-{(E)-3-[4-(benzyloxy)-3-nitrophenyl]-2-propenoyl}-2-hydroxy-5-methylphenyl)acetamide 2-Hydroxy-5-methyl-3-acetamidoacetophenone (600 mg, 2.89 mmol) and 4-benzyloxy-3-nitrobenzaldehyde (890 mg, 3.46 mmol) were reacted according to the same procedure as Preparation 1 to give 590 mg (Yield 46%) of the title compound.

$^1$H NMR (CDCl$_3$, ppm); δ8.48 (1H, s), 8.19 (1H, s), 7.84–7.70 (3H, m), 7.60–7.00 (9H, m), 5.31 (2H, s), 2.41 (3H, s), 2.23 (3H, s)

FAB MS (m/e)=447[M$^+$+1]

Preparation 4
Synthesis of N-{2-[4-(benzyloxy)-3-nitrophenyl]-3-hydroxy-6-methyl-4-oxo-4H-chromen-8-yl}acetamide The compound prepared in Preparation 3 (590 mg, 1.32 mmol) was reacted according to the same procedure as Preparation 2 to give 340 mg (Yield 56%) of the title compound.

$^1$H NMR (DMSO-$d_6$, ppm); δ9.99 (2H, br s), 8.77 (1H, s), 8.53 (1H, d), 7.77–7.40 (7H, m), 5.44 (2H, s), 2.42 (3H, s), 2.19 (3H, s)

FAB MS (m/e)=461[M$^+$+1]

EXAMPLE 3
Synthesis of N-[2-(4-hydroxy-3-nitrophenyl)-3-hydroxy-6-methyl-4-oxo-4H-chromen-8-yl]acetamide (Compound 3)

The compound prepared in Preparation 4 (15 mg, 32 μmol) was reacted according to the same procedure as Example 2 to give 10 mg (Yield 83%) of the title compound.

$^1$H NMR (DMSO-$d_6$, ppm); δ11.65(1H, br s), 9.97 (1H, s), 9.86 (1H, s), 8.78 (1H, s), 8.42 (1H, d), 7.74 (2H, d), 7.32 (1H, d), 2.42 (3H, s), 2.19 (3H, s)

FAB MS (m/e)=371[M$^+$+1]

Preparation 5
Synthesis of (E)-3-[4-(benzyloxy)phenyl]-1-(2-hydroxy-5-methyl-3-nitrophenyl)-2-propen-1-one 2-Hydroxy-5-methyl-3-nitroacetophenone (100 mg, 0.51 mmol) and 4-benzyloxybenzaldehyde (100 mg, 0.47 mol) were reacted according to the same procedure as Preparation 1 to give 150 mg (Yield 75%) of the title compound.

$^1$H NMR (CDCl$_3$, ppm); δ8.19 (1H, s), 7.84–7.70 (4H, m), 7.60–7.00 (9H, m), 5.31 (2H, s), 2.41 (3H, s)

FAB MS (m/e)=390[M$^+$+1]

Preparation 6
Synthesis of 2-[4-(benzyloxy)phenyl]-3-hydroxy-6-methyl-8-nitro-4H-chromen-4-one The compound prepared in Preparation 5 (150 mg, 0.38 mmol) was reacted according to the same procedure as Preparation 2 to give 80 mg (Yield 51%) of the title compound.

$^1$H NMR (DMSO-$d_6$, ppm); δ8.39 (1H, s), 8.25 (3H, m), 7.60–7.20 (7H, m), 5.22 (2H, s), 2.52 (3H, s)

FAB MS (m/e)=404[M$^+$+1]

EXAMPLE 4
Synthesis of 8-amino-2-(4-hydroxyphenyl)-3-hydroxy-6-methyl-4H-chromen-4-one (Compound 4)

The compound prepared in Preparation 6 (20 mg, 49.6 μmol) was reacted according to the same procedure as Example 1 to give 11.9 mg (Yield 85%) of the title compound.

$^1$H NMR (DMSO-$d_6$, ppm); δ10.03 (1H, br s), 9.10 (1H, br s), 8.21 (2H, d), 7.03 (1H, s), 6.92 (2H, d), 6.83 (1H, s), 5.58 (2H, br s), 2.29 (3H, s)

FAB MS (m/e)=284[M$^+$+1]

Preparation 7
Synthesis of (E)-3-[4-(benzyloxy)-3-nitrophenyl]-1-(2-hydroxy-5-methylphenyl)-2-propen-1-one 2-Hydroxy-5-methylacetophenone (200 mg, 1.33 mol) and 4-benzyloxy-3-nitrobenzaldehyde (350 mg, 1.36 mmol) were reacted according to the same procedure as Preparation 1 to give 170 mg (Yield 29%) of the title compound.

$^1$HMR (CDCl$_3$, ppm); δ8.19 (1H, s), 7.84–7.70 (4H, m), 7.60–7.00 (9H, m), 5.31 (2H, s), 2.41 (3H, s)

FAB MS (m/e)=390[M$^+$+1]

Preparation 8
Synthesis of 2-[4-(benzyloxy)-3-nitrophenyl]-3-hydroxy-6-methyl-4H-chromen-4-one The compound prepared in Preparation 7 (170 mg, 0.43 mmol) was reacted according to the same procedure as Preparation 2 to give 90 mg (Yield 51%) of the title compound.

$^1$H NMR (DMSO-$d_6$, ppm); δ9.90 (1H, br s), 8.75 (1H, s), 8.48 (1H, s), 7.90 (1H, s), 7.80–7.30 (8H, m), 5.43 (2H, s), 2.45 (3H, s)

FAB MS (m/e)=404[M$^+$+1]

EXAMPLE 5
Synthesis of 2-(3-amino-4-hydroxyphenyl)-3-hydroxy-6-methyl-4H-chromen-4-one (Compound 5)

The compound prepared in Preparation 8 (25 mg, 62 μmol) was reacted according to the same procedure as Example 1 to give 17 mg (Yield 96%) of the title compound.

1H NMR (DMSO-$d_6$, ppm); δ10.05 (1H, s), 9.10 (1H, s), 7.87 (1H, s), 7.58 (4H, m), 7.50 (1H, m), 7.30 (1H, m), 6.83 (1H, d), 2.44 (3H, s)

FAB MS (m/e)=284[M$^+$+1]

EXAMPLE 6
Synthesis of N-[2-hydroxy-5-(3-hydroxy-6-methyl-4-oxo-4H-chromen-2-yl)phenyl]acetamide (Compound 6)

The compound prepared in Example 5 (10 mg, 35 μmol) was dissolved in dichloromethane (2 ml) and reacted with excess acetic anhydride for 1 hour at room temperature. The mixture was concentrated and the residue was purified by silica gel column chromatography (eluent: 50% ethylacetate/hexane) to give 5 mg (Yield 44%) of the title compound.

¹H NMR (DMSO-d₆, ppm); δ10.43 (1H, s), 9.46 (1H, s), 9.26 (1H, s), 8.54 (1H, s), 7.88 (2H, m), 7.59 (2H, s), 7.03 (1H, m), 2.44 (3H, s), 2.23 (3H, s)

FAB MS (m/e)=326[M⁺+1]

EXAMPLE 7

Synthesis of N-{2-[4-hydroxy-3-(isopropylamino)phenyl]-3-hydroxy-6-methyl-4-oxo-4H-chromen-8-yl}acetamide (Compound 7A) and N-[2-(3-amino-4-hydroxy-phenyl)-3-hydroxy-6-methyl-4oxo-4H-chromen-8-yl]acetamide (Compound 7B)

The compound prepared in Preparation 4 (30 mg, 65 μmol) was dissolved in 20% ethanol/dichloromethane (5 ml) and acetone (1 ml) and reacted under 10% Pd/C catalyst and hydrogen pressure of 50 psi for 3 hours. The reaction solution was filtered through a cellite pad, concentrated, and purified by silica gel column chromatography (eluent: 70% ethylacetate/hexane) to give 13 mg (Yield 52%) of the title compound 7A and 7 mg (Yield 31%) of the title compound 7B.

Compound 7A

¹H NMR (CDCl₃, ppm); δ8.09 (1H, s), 7.62 (1H, s), 7.40–7.20 (5H, m), 6.76 (1H, d), 2.36 (3H, s), 2.18 (3H, s), 1.93 (1H, m), 1.17 (6H, m)

FAB MS (m/e)=383[M⁺+1]

Compound 7B

¹H NMR (DMSO-d₆, ppm); δ9.78 (1H, s), 9.10 (1H, br s), 7.73 (1H, s), 7.67 (1H, s), 7.55 (1H, s), 7.41 (1H, d), 6.81 (1H, d), 2.41 (3H, s), 2.19 (3H, s)

FAB MS (m/e)=341[M⁺+1]

Preparation 9

Synthesis of (E)-3-(3-fluoro-4-methoxyphenyl)-1-(2-hydroxy-5-methyl-3-nitrophenyl)-2-propen-1-one 2-Hydroxy-5-methyl-3-nitroacetophenone (100 mg, 0.51 mmol) and 4-methoxy-3-fluorobenzaldehyde (95 mg, 0.61 mmol) were reacted according to the same procedure as Preparation 1 to give 127 mg (Yield 74%) of the title compound.

¹H NMR (DMSO-d₆, ppm); δ8.54 (1H, d), 8.40–8.20 (3H, m), 7.28 (3H, m), 3.89 (3H, s), 2.48 (3H, s)

FAB MS (m/e)=332[M⁺+1]

Preparation 10

Synthesis of 2-(3-fluoro-4-methoxyphenyl)-3-hydroxy-6-methyl-8-nitro-4H-chromen-4-one The compound prepared in Preparation 9 (127 mg, 0.38 mmol) was reacted according to the same procedure as Preparation 2 to give 80 mg (Yield 60%) of the title compound.

¹H NMR(DMSO-d6, ppm); δ8.54 (1H, d), 8.40–8.20 (3H, m), 7.28 (1H, m), 3.89 (3H, s), 2.48 (3H s)

FAB MS (m/e)=346[M⁺+1]

EXAMPLE 8

Synthesis of 2-(3-fluoro-4-hydroxyphenyl)-3-hydroxy-6-methyl-8-nitro-4H-chromen-4-one (Compound 8)

The compound prepared in Preparation 10 (80 mg, 0.23 mmol) was reacted according to the same procedure as Example 2 to give 44 mg (Yield 57%) of the title compound.

¹H NMR (DMSO-d₆, ppm); δ8.39 ((1H, s), 8.26 (1H, s), 8.03 (1H, d), 7.97 (1H, d), 7.13 (1H, m), 2.41 (3H, s)

FAB MS (m/e)=332[M⁺+1]

EXAMPLE 9

Synthesis of 8-amino-2-(3-fluoro-4-hydroxyphenyl)-3-hydroxy-6-methyl-4H-chromen-4one (Compound 9)

The compound prepared in Example 8 (11 mg, 33 μmol) was reacted according to the same procedure as Example 1 to give 7.7 mg (Yield 77%) of the title compound.

¹H NMR (DMSO-d₆, ppm); δ8.15 (1H, d), 8.02 (1H, d), 7.02 (3H, m), 6.82 (1H, s), 5.62 (2H, s), 2.29 (3H, s)

FAB MS (m/e)=302[M⁺+1]

Preparation 11

Synthesis of 3-(benzyloxy)-2-[4-(benzyloxy)-3-nitrophenyl]-6-methyl-8-nitro-4H-chromen-4-one The compound prepared in Preparation 2 (100 mg, 0.22 mmol) was refluxed with 1.5 equivalent of benzylbromide and 2 equivalents of potassium carbonate in acetone for 10 hours. After the mixture was cooled to room temperature, it was filtered and concentrated. The residue was then dissolved in ethylacetate and washed with excess water and diethylether to give 100 mg (Yield 84%) of the title compound.

¹H NMR(DMSO-d6, ppm); δ8.62 (1H, s), 8.45 (1H, s), 8.30 (1H, s), 8.27 (1H, s), 7.69 (1H, d), 7.50–7.28 (1H, m), 5.44 (2H, s), 5.18 (2H, s), 2.54 (3H, s)

FAB MS (m/e)=539[M⁺+1]

Preparation 12

Synthesis of 8-amino-2-[3-amino-4-(benzyloxy)phenyl]-3-(benzyloxy)-6-methyl-4H-chromen-4-one The compound prepared in Preparation 11 (100 mg, 0.18 mmol) was dissolved in acetonitrile (5 ml) and water (1 ml). Sodium hydrosulfite (370 mg) and sodium bicarbonate (310 mg) were added and the resulting mixture was stirred for 6 hours at room temperature. After concentration, the residue was washed with water (5 ml) and dichloromethane (1 ml) to give 35 mg (Yield 40%) of the title compound.

¹H NMR (CDCl₃, ppm); δ7.46–7.25 (13H, m), 6.90 (1H, d), 6.83 (1H, s), 5.16 (2H, s), 5.08 (2H, s), 2.37 (3H, s)

FAB MS (m/e)=479[M⁺+1]

Preparation 13

Synthesis of N-[5-[8-(ureido)-3-(benzyloxy)-6-methyl-4-oxo-4H-chromen-2-yl]-2-(benzyloxy)phenyl]urea The compound prepared in Preparation 12 (35 mg, 73 μmol) was dissolved in dichloromethane (20 ml), triethylamine (0.1 ml) and triphosgene (80 ml) were added at 0° C. and then stirred. After 1 hour, aqueous ammonia (0.3 ml) was added and the resulting mixture was stirred for 30 minutes and then concentrated. The residue was dissolved in ethylacetate (15 ml), washed with water (15 ml), and then concentrated. The residue was washed with dichloromethane and 10% methanol/dichloromethane solution to give 25 mg (Yield 60%) of the title compound.

¹H NMR (CDCl₃, ppm); δ9.20 (1H, s), 8.76 (1H, s), 8.15 (2H, d), 8.05 (1H, s), 7.75 (H, d), 7.48–7.18 (1H, m), 6.92 (1H, d), 6.50 (2H, s), 6.32 (2H, s), 5.31 (2H, s), 5.16 (2H, s), 2.39 (3H, s)

FAB MS (m/e)=565 [M⁺+1]

EXAMPLE 10

Synthesis of N-{5-[8-(ureido)-3-hydroxy-6-methyl-4-oxo-4H-chromen-2-yl]-2-hydroxyphenyl}urea (Compound 10)

The compound prepared in Preparation 13 (25 mg, 44.3 μmol) was reacted according to the same procedure as Example 2 to give 10 mg (Yield 59%) of the title compound.

¹H NMR (DMSO-d₆, ppm); δ10.73 (1H, s), 9.24 (1H, s), 8.80 (1H, s), 8.18 (2H, d), 8.05 (1H, s), 7.75 (1H, d), 7.45 (1H, s), 6.96 (1H, d), 6.59 (2H, s), 6.34 (2H, s), 2.39 (3H, s)

FAB MS (m/e)=385[M⁺+1]

Preparation 14

Synthesis of (E)-1-(2-hydroxy-5-methyl-3-nitrophenyl)-3-(4-nitrophenyl)-2-propen-1-one 2-Hydroxy-3-nitro-5-methylacetophenone (100 mg, 0.51 mmol) and 4-nitrobenzaldehyde (116 mg, 0.76 mmol) were reacted according to the same procedure as Preparation 1 to give 155 mg (Yield 92%) of the title compound.

¹H NMR (DMSO-d₆, ppm); δ8.36 (1H, s), 8.32 (2H, d), 8.19 (2H, d), 8.10 (2H, m), 7.93 (1H, d), 2.40 (3H, s)

FAB MS (m/e)=329[M⁺+1]

Preparation 15

Synthesis of 3-hydroxy-6-methyl-8-nitro-2-(4-nitrophenyl)-4H-chromen-4-one

The compound prepared in Preparation 14 (155 mg, 0.47 mmol) was reacted according to the same procedure as Preparation 2 to give 31 mg (Yield 19%) of the title compound.

¹H NMR (DMSO-d₆, ppm); δ10.80 (1H, br s), 8.50–8.20 (6H, m), 2.52 (3H, s)

FAB MS (m/e)=343[M⁺+1]

EXAMPLE 11

Synthesis of 8-amino-2-(4-aminophenyl)-3-hydroxy-6-methyl-4H-chromen-4-one (Compound 11)

The compound prepared in Preparation 15 (31 mg, 90 μmol) was reacted according to the same procedure as Example 1 to give 7.3 mg (Yield 27%) of the title compound.

¹H NMR (DMSO-d₆, ppm); δ8.06 (2H, d), 7.61 (1H, s), 7.02 (1H, s), 6.81 (1H, s), 6.66 (2H, d), 5.51 (2H, br s), 2.28 (3H, s)

FAB MS (m/e)=283[M⁺+1]

Preparation 16

Synthesis of (E)-3-[3-(benzyloxy)phenyl]-1-(2-hydroxy-5-methyl-3-nitrophenyl)-2-propen-1-one 2-Hydroxy-3-nitro-5-methylacetophenone (100 mg, 0.51 mmol) and 3-benzyloxybenzaldehyde (140 mg, 0.66 mmol) were reacted according to the same procedure as Preparation 1 to give 170 mg (Yield 85%) of the title compound. ¹H NMR (CDCl₃, ppm); δ8.42 (1H, s), 8.28 (1H, s), 7.94 (1H, s), 7.89 (1H, d), 7.60–7.30 (6H, m), 7.18 (3H, m), 5.19 (2H, s), 2.52 (3H, s)

FAB MS (m/e)=390[M⁺+1]

Preparation 17

Synthesis of 2-[3-(benzyloxy)phenyl]-3-hydroxy-6-methyl-8-nitro-4H-chromen-4-one The compound prepared in Preparation 16 (170 mg, 0.43 mmol) was reacted according to the same procedure as Preparation 2 to give 90 mg (Yield 51%) of the title compound.

¹H NMR (DMSO-d₆, ppm); δ10.20 (1H, br s), 8.42 (1H, s), 8.28 (1H, s), 7.94 (1H, s), 7.89 (1H, d), 7.60–7.30 (6H, m), 7.18 (1H, d), 5.19 (2H, s), 2.52 (3H, s)

FAB MS (m/e)=404[M⁺+1]

EXAMPLE 12

Synthesis of 8-amino-3-hydroxy-2-(3-hydroxyphenyl)-6-methyl-4H-chromen-4-one (Compound 12)

The compound prepared in Preparation 17 (20 mg, 0.05 mol) was reacted according to the same procedure as Example 1 to give 13 mg (Yield 91%) of the title compound.

¹H NMR (DMSO-d₆, ppm); δ9.62 (1H, s), 9.31 (1H, br s), 7.74 (2H, m), 7.33 (1H, t), 7.06 (1H, s), 6.87 (2H, m), 5.54 (2H, br s), 2.30 (3H, s)

FAB MS (m/e)=284[M⁺+1]

Preparation 18

Synthesis of (E)-3-[2-(benzyloxy)-3,4-dimethoxyphenyl]-1-(2-hydroxy-5-methylphenyl)-2-propen-1-one 2-Hydroxy-5-methylacetophenone (690 mg, 2.53 mmol) and 2-benzyloxy-3,4-dimethoxybenzaldehyde (460 mg, 3.03 mmol) was reacted according to the same procedure as Preparation 1 to give 740 mg (Yield 76%) of the title compound.

¹H NMR (CDCl₃, ppm); δ10.10 (1H, s), 8.01 (1H, s), 7.72 (1H, d), 7.65–7.24 (7H, m), 6.90 (1H, d), 6.76 (1H, d), 5.21 (1H, s), 5.12 (2H, s), 3.93 (6H, s), 2.22 (3H, s)

FAB MS (m/e)=405[M⁺+1]

Preparation 19

Synthesis of 2-[2-(benzyloxy)-3,4-dimethoxyphenyl]-3-hydroxy-6-methyl-4H-chromen-4one The compound prepared in Preparation 18 (740 mg, 1.9 mmol) was reacted according to the same procedure as Preparation 2 to give 370 mg (Yield 47%) of the title compound.

¹H NMR (DMSO-d₆, ppm); δ7.90 (1H, s), 7.55 (1H, d), 7.44 (1H, d), 7.27 (1H, d), 7.25–7.14 (5H, m), 5.07 (2H, s), 3.89 (3H, s), 3.82 (3H, s), 2.43 (3H, s)

FAB MS (m/e)=419[M⁺+1]

EXAMPLE 13

Synthesis of 3-hydroxy-6-methyl-2-(2,3,4-trihydroxyphenyl)-4H-chromen-4-one (Compound 13)

The compound prepared in Preparation 19 (13 mg, 0.03 mmol) was reacted according to the same procedure as Example 2 to give 5 mg (Yield 53%) of the title compound.

¹H NMR (CD₃OD, ppm); δ7.96 (1H, s), 7.58 (1H, d), 7.51 (1H, d), 7.07 (1H, d), 6.56 (1H, d), 2.47 (3H, s)

FAB MS (m/e)=301[M⁺+1]

Preparation 20

Synthesis of (E)-3-(2-bromo-3,4-dimethoxyphenyl)-1-(2-hydroxy-5-methylphenyl)-2-propen-1-one 2-Hydroxy-5-methylacetophenone (85 mg, 0.57 mmol) and 2-bromo-3,4-dimethoxybenzaldehyde (166 mg, 0.68 mmol) were reacted according to the same procedure as Preparation 1 to give 140 mg (Yield 54.6%) of the title compound.

1H NMR (CD₃OD, ppm); δ7.93 (1H, s), 7.58 (1H, d), 7.52 (1H, d), 7.35 (1H, s), 7.18 (1H, s), 6.77 (1H, d), 6.52 (1H, d), 3.91 (3H, s), 3.79 (3H, s), 2.46 (3H, s)

FAB MS (m/e)=377 [M⁺+1]

Preparation 21

Synthesis of 2-(2-bromo-3,4-dimethoxyphenyl)-3-hydroxy-6-methyl-4H-chromen-4-one The compound prepared in Preparation 20 (130 mg, 0.34 mmol) was reacted according to the same procedure as Preparation 2 to give 82 mg (Yield 61.7%) of the title compound.

¹H NMR (CD₃OD, ppm); δ7.94 (1H, s), 7.60 (1H, d), 7.53 (1H, d), 7.38 (1H, s), 7.23 (1H, s), 3.91 (3H, s), 3.79 (3H, s), 2.46 (3H, s)

FAB MS (m/e)=392[M⁺+1]

EXAMPLE 14

Synthesis of 2-(2-bromo-3,4-dihydroxyphenyl)-3-hydroxy-6-methyl-4H-chromen-4-one (Compound 14)

The compound prepared in Preparation 21 (30 mg, 77 μmmol) was reacted according to the same procedure as Example 2 to give 18 mg (Yield 64.4%) of the title compound.

1H NMR (CD₃OD, ppm); δ7.92 (1H, s), 7.57 (1H, d), 7.49 (1H, d), 6.90–6.88 (2H, m), 2.45 (3H, s)

FAB MS (m/e)=363[M⁺+1]

Preparation 22

Synthesis of N-(3-{(E)-3-[4-(benzyloxy)-3-bromophenyl]-2-propenoyl}-2-hydroxy-5-methylphenyl)acetamide 2-Hydroxy-5-methyl-3-acetamidoacetophenone (1.7 g, 8.2 mmol), 4-benzyloxy-3-bromobenzaldehyde (2.6 g, 8.9 mmol) and 3 equivalents of sodium hydroxide (120 mg) were introduced into 80% aqueous ethanol solution and stirred for 3 hours at room temperature. The reaction solution was acidified by 2N hydrochloric acid solution and diluted with water. The resulting solid was filtered, washed with large amount of water and methanol, and then dried to give 3.09 g (Yield 78%) of the title compound as a yellow solid.

$^1$H NMR (CDCl$_3$, ppm); δ8.62 (1H, s), 8.15–7.90 (3H, m), 7.80–7.30 (10H, m), 7.13 (1H, d), 5.38 (2H, s), 2.53 (3H, s), 2.38 (3H, s)

FAB MS (m/e)=480[M$^+$+1]

Preparation 23

Synthesis of N-{2-[4-(benzyloxy)-3-bromophenyl]-3-hydroxy-6-methyl-4-oxo-4H-chromen-8-yl}acetamide The compound prepared in Preparation 22 (3.09 g, 6.45 mmol) was introduced into methanol and then aqueous hydrogen peroxide (0.5 ml) and 10% aqueous sodium hydroxide solution (0.5 ml) were added at room temperature. The mixture was stirred for 2 hours at room temperature, acidified by 2N hydrochloric acid solution, and diluted with water. The resulting solid having a pale yellow color was filtered, washed with large amount of water and methanol, and then dried to give 2.96 g (Yield 93%) of the title compound.

$^1$H NMR (DMSO-d$_6$, ppm); δ9.99 (1H, br s), 9.80 (1H, br s), 8.49 (1H, s), 8.27 (1H, s), 7.74 (2H, m), 7.60–7.30 (8H, m), 5.33 (2H, s), 2.42 (3H, s), 2.19 (3H, s)

FAB MS (m/e)=494[M$^+$+1]

Preparation 24

Synthesis of N-{3-(benzyloxy)-2-[4-(benzyloxy)-3-bromophenyl]-6-methyl-4-oxo-4H-chromen-8-yl}acetamide The compound prepared in Preparation 23 (2.96 g, 6 mmol) was refluxed with 1.5 equivalent of benzylbromide and 2 equivalents of potassium carbonate in acetone for 10 hours. After the reaction mixture was cooled to room temperature, it was filtered and concentrated. The residue was dissolved in ethylacetate and washed with large amount of water and diethylether to give 1.96 g (Yield 56%) of the title compound.

$^1$H NMR (DMSO-d$_6$, ppm); δ8.37 (1H, s), 8.06 (1H, s), 7.79 (2H, m), 7.60–7.20 (5H, m), 6.96 (1H, d), 5.25 (2H, s), 5.11 (2H, s), 2.46 (3H, s), 2.28 (3H, s)

FAB MS (m/e)=584[M$^+$+1]

Preparation 25

Synthesis of 8-amino-3(benzyloxy)-2-[4-(benzyloxy)-3-bromophenyl]-6-methyl-4H-chromen-4-one The compound prepared in Preparation 24 (1.96 g, 3.36 mmol) was dissolved in dichloromethane (200 ml), di(t-butyl)dicarbonate (0.9 g) and catalytic amount of dimethylaminopyridine were added, and the resulting mixture was stirred for 7 hours at room temperature. After completion of reaction, the solution was concentrated. The residue was dissolved in methanol (100 ml) and 2.5 N aqueous sodium hydroxide solution (5 ml) was added thereto. The resulting mixture was stirred for 10 minutes at room temperature and concentrated. The residue was dissolved in ethylacetate, washed with water, and the extract was concentrated. The residue was dissolved in a solvent mixture of dichloromethane and trifluoroacetic acid (1:1, v/v), reacted for 2 hours at room temperature, and then concentrated under reduced pressure to give 1.6 g (Yield 88%) of the title compound.

$^1$H NMR (DMSO-d$_6$, ppm); δ8.35 (1H, s), 8.11 (1H, d), 7.51–7.28 (1H, m), 7.06 (1H, s), 6.87 (1H, s), 5.34 (2H, s), 5.07 (2H, s), 2.31 (3H, s)

FAB MS (m/e)=542[M$^+$+1]

Preparation 26

Synthesis of 2-{3-(benzyloxy)-2-[4-(benzyloxy)-3-bromophenyl]-6-methyl-4-oxo-4H-chromen-8-yl)}-1λ$^6$-isothiazolidin-1,1-dione The compound prepared in Preparation 25 (100 mg, 0.18 mmol) was dissolved in dichloromethane (5 ml), 2.5 equivalents of 3 -chloropropanesulfonylchloride, 3 equivalents of triethylamine and catalytic amount of dimethylaminopyridine were added thereto, and the resulting mixture was reacted for 2 hours at room temperature. The reaction mixture was concentrated under reduced pressure and the residue was dissolved in dimethylformamide (5 ml). 1N aqueous sodium hydroxide solution (2 ml) was added and the resulting mixture was reacted for 30 minutes at 50° C., acidified by 2N hydrochloric acid solution and diluted with water. The resulting solid was filtered and washed with large amount of water and diethylether to give 80 mg (Yield 67%) of the title compound.

$^1$H NMR (CDCl$_3$, ppm); δ8.32 (1H, s), 8.04 (2H, d), 7.63–6.97 (12H, m), 5.23 (2H, s), 5.08 (2H, s), 3.84 (2H, t), 3.41 (2H, t), 2.61 (2H, m), 2.47 (3H, s)

FAB MS (m/e)=646[M$^+$+1]

EXAMPLE 15

Synthesis of 2-[3-hydroxy-2-(4-hydroxyphenyl)-6-methyl-4-oxo-4H-chromen-8-yl]-1λ$^6$-isothiazolidin-1,1-dione (Compound 15)

The compound prepared in Preparation 26 (30 mg, 46.51 μmol) was dissolved in 10% methanol/dichloromethane solvent, catalytic amount of 10% Pd/C was added, and the resulting mixture was reacted under hydrogen pressure of 50 psi for 2 hours. The mixture was filtered through a cellite pad and the filtrate was concentrated to give 14.8 mg (Yield 82%) of the title compound.

$^1$H NMR (DMSO-d$_6$, ppm); δ10.10 (1H, s), 9.40 (1H, s), 8.13 (2H, d), 7.87 (1H, s), 7.68 (1H, s), 6.94 (2H, d), 3.87 (2H, t), 3.49 (2H, t), 2.55 (2H, m), 2.45 (3H, s)

FAB MS (m/e)=388[M$^+$+1]

Preparation 27

Synthesis of (E)-3-(3-fluoro-4-methoxyphenyl)-1-(2-hydroxy-5-methyl-3-nitrophenyl)-2-propen-1-one 2-Hydroxy-5-methyl-3-nitroacetophenone (100 mg, 0.51 mmol) and 4-methoxy-3-fluorobenzaldehyde (95 mg, 0.61 mmol) were reacted according to the same procedure as Preparation 22 to give 127 mg (Yield 74%) of the title compound.

$^1$H NMR (DMSO-d$_6$, ppm); δ8.54 (1H, d), 8.40–8.20 (3H, m), 7.28 (3H, m), 3.89 (3H, s), 2.48 (3H, s)

FAB MS (m/e)=332[M$^+$+1]

Preparation 28

Synthesis of 2-(3-fluoro-4-methoxyphenyl)-3-hydroxy-6-methyl-8-nitro-4H-chromen-4-one The compound prepared in Preparation 27 (127 mg, 0.38 mmol) was reacted according to the same procedure as Preparation 23 to give 80 mg (Yield 60%) of the title compound.

$^1$H NMR (DMSO-d$_6$, ppm); δ8.54 (1H, d), 8.40–8.20 (3H, m), 7.28 (1H, m), 3.89 (3H, s), 2.48 (3H, s)

FAB MS (m/e)=346[M$^+$+1]

Preparation 29

Synthesis of 2-(3-fluoro-4hydroxyphenyl)-3-hydroxy-6-methyl-8-nitro-4H-chromen-4-one The compound prepared in Preparation 28 (80 mg, 0.23 mmol) was dissolved in dichloromethane (10 ml), excess borontribromide was added thereto, and the resulting mixture was reacted for 2 hours at room temperature. The remaining borontribromide was decomposed by methanol and concentrated under reduced pressure. The solid thus produced was washed with dichloromethane to give 44 mg (Yield 57%) of the title compound.

$^1$H NMR (DMSO-d$_6$, ppm); δ8.39 ((1H, s), 8.26 (1H, s), 8.03 (1H, d), 7.97 (1H, d), 7.13 (1H, m), 2.41 (3H, s)

FAB MS (m/e)=332[M$^+$+1]

Preparation 30

Synthesis of 3-(benzyloxy)-2-[4-(benzyloxy)-3-fluorophenyl]-6-methyl-8-nitro-4H-chromen-4-one The compound prepared in Preparation 29 (30 mg, 90 μmol) was reacted according to the same procedure as Preparation 24 to give 15.8 mg (Yield 34%) of the title compound.

$^1$H NMR (CDCl$_3$, ppm); δ8.34 (1H, s), 8.20 (1H, s), 8.05 (1H, d), 7.96 (1H, d), 7.47–7.25 (10H, m), 7.06 (1H, m), 5.23 (2H, s), 5.20 (2H, s), 2.55 (3H, s)

FAB MS (m/e)=512[M$^+$+1]

Preparation 31

Synthesis of 8-amino-3-(benzyloxy)-2-[4-(benzyloxy)-3-fluorophenyl]-6-methyl-4H-chromen-4-one The compound prepared in Preparation 30 (15 mg, 29 μmol), 10 equivalents of iron and 3 drops of conc. hydrochloric acid were introduced into ethanol (5 ml) and then refluxed for 1 hour. The reaction solution was concentrated, and the residue was dissolved in ethylacetate and filtered through a cellite pad to remove any insoluble substances. The organic extract was filtered through a silica gel pad and the filtrate was concentrated to give 10 mg (Yield 71%) of the title compound:

$^1$H NMR (CDCl$_3$, ppm); δ8.19 (1H, s), 8.06 (1H, d), 7.50–7.28 (12H, m), 7.10 (1H, s), 6.86 (1H, s), 5.64 (2H, br s), 5.34 (2H, s), 5.07 (2H, s), 2.30 (3H, s)

FAB MS (m/e)=482[M$^+$+1]

Preparation 32

Synthesis of 2-{3-(benzyloxy)-2-[4-(benzyloxy)-3-fluorophenyl]-6-methyl-4-oxo-4H-chromen-8-yl}-1λ$^6$-isothiazolidin-1,1-dione The compound prepared in Preparation 31 (10 mg, 20 μmol) was reacted according to the same procedure as Preparation 26 to give 7 mg (Yield 58%) of the title compound.

$^1$H NMR (CDCl$_3$, ppm); δ8.05 (3H, m), 7.70–7.20 (12H, m), 5.23 (4H, m), 3.89 (2H, t), 3.43 (2H, t), 2.65 (2H, m), 2.47 (3H, s)

FAB MS (m/e)=586[M$^+$+1]

EXAMPLE 16

Synthesis of 2-[2-(3-fluoro-4-hydroxyphenyl)-3-hydroxy-6-methyl-4-oxo-4H-chromen-8-yl]-1λ$^6$-isothiazolidin-1,1-dione (Compound 16)

The compound prepared in Preparation 32 (5 mg, 8.5 μmol) was reacted according to the same procedure as Example 15 to give 2.6 mg (Yield 76%) of the title compound.

$^1$H NMR (CDCl$_3$, ppm); δ8.10 (1H, d), 7.95 (1H, d), 7.85 (1H, s), 7.69 (1H, s), 7.10 (1H, m), 3.88 (2H, t), 3.49 (2H, t), 2.53 (2H, m), 2.44 (3H, s)

FAB MS (m/e)=406[M$^+$+1]

Preparation 33

Synthesis of (E)-3-[4-(benzyloxy)-3-chlorophenyl]-1-(2-hydroxy-5-methyl-3-nitrophenyl)-2-propen-1-one 2-Hydroxy-5-methyl-3-nitroacetophenone (750 mg, 3.84 mmol) and 4-benzyloxy-3-chlorobenzaldehyde (1 g, 3.84 mmol) were reacted according to the same procedure as Preparation 15 to give 970 mg (Yield 59%) of the title compound.

$^1$H NMR (CDCl$_3$, ppm); δ8.03 (1H, s), 7.92(1H, s), 7.76 (2H, m), 7.50–7.39 (7H, m), 7.00 (1H, d), 5.23 (2H, s), 2.42 (3H, s)

FAB MS (m/e)=424[M$^+$+1]

Preparation 34

Synthesis of 2-[4-(benzyloxy)-3-chlorophenyl]-3-hydroxy-6-methyl-8-nitro-4H-chromen-4one The compound prepared in Preparation 33 (970 mg, 2.29 mmol) was reacted according to the same procedure as Preparation 23 to give 590 mg (Yield 59%) of the title compound.

$^1$H NMR (DMSO-d$_6$, ppm); δ8.41 (1H, s), 8.38 (1H, s), 8.27(1H, s), 8.21 (1H, d), 7.50–7.41 (11H, m), 5.33 (2H, s), 2.53 (3H, s)

FAB MS (m/e)=438[M$^+$+1]

Preparation 35

Synthesis of 3-(benzyloxy)-2-[4-(benzyloxy)-3-chlorophenyl]-6-methyl-8-nitro-4H-chromen-4-one The compound prepared in Preparation 34 (590 mg, 1.35 mmol) was reacted according to the same procedure as Preparation 24 to give 340 mg (Yield 47%) of the title compound.

$^1$H NMR (DMSO-d$_6$, ppm); δ8.43 (1H, s), 8.28 (1H, s), 8.20 (1H, s), 8.05 (1H, d), 7.49–7.31 (11H, m), 5.33 (2H, s), 5.16 (2H, s), 2.53 (3H, s)

FAB MS (m/e)=528[M$^+$+1]

Preparation 36

Synthesis of 8-amino-3-(benzyloxy)-2-[4-(benzyloxy)-3-chlorophenyl]-6-methyl-4H-chromen-4-one The compound prepared in Preparation 35 (100 mg, 189 μmol) was reacted according to the same procedure as Preparation 31 to give 49.7 mg (Yield 52%) of the title compound.

$^1$H NMR (DMSO-d$_6$, ppm); δ8.19 (1H, s), 8.06 (1H, d), 7.50–7.28 (11H, m), 7.10 (1H, s), 6.86 (1H, s), 5.64 (2H, br s), 5.34 (2H, s), 5.07 (2H, s), 2.30 (3H, s)

FAB MS (m/e)=498[M$^+$+1]

Preparation 37

Synthesis of 2-{3-(benzyloxy)-2-[4-(benzyloxy)-3-chlorophenyl]-6-methyl-4-oxo-4H-chromen-8-yl}-1λ$^6$-isothiazolidin-1,1-dione The compound prepared in Preparation 36 (49.7 mg, 100 μmol) was reacted according to the same procedure as Preparation 26 to give 49.4 mg (Yield 82%) of the title compound.

$^1$H NMR (DMSO-d$_6$, ppm); δ8.20 (1H, s), 8.10 (1H, d), 7.90 (1H, s), 7.73 (1H, s), 7.51–7.30 (11H, m), 5.32 (2H, s), 5.10 (2H, s), 3.86 (2H, t), 3.47 (2H, t), 2.50 (2H, m), 2.46 (3H, s)

FAB MS (m/e)=602[M$^+$+1]

EXAMPLE 17

Synthesis of 2-[2-(3-chloro-4-hydroxyphenyl)-3-hydroxy-6-methyl-4-oxo-4H-chromen-8-yl]-1λ$^6$-isothiazolidin-1,1-dione (Compound 17)

The compound prepared in Preparation 37 (20 mg, 33 μmol) was dissolved in dichloromethane solvent(5 ml), catalytic amount of 10% Pd/C was added thereto, and the resulting mixture was reacted under hydrogen pressure of 1 atm for 10 hours. The reaction solution was filtered through a cellite pad and concentrated to give 8.2 mg (Yield 58%) of the title compound.

$^1$H NMR (DMSO-d$_6$, ppm); δ8.30 (1H, s), 8.08(1H, d), 7.86 (1H, s), 7.67 (1H, s), 7.11 (1H, d), 3.88 (2H, t), 3.49 (2H, t), 2.54 (2H, m), 2.45 (3H, s)

FAB MS (m/e)=422[M$^+$+1]

EXAMPLE 18

Synthesis of 2-[2-(3-bromo-4hydroxyphenyl)-3-hydroxy-6-methyl-4-oxo-4H-chromen-8-yl]-1$\lambda^6$-isothiazolidin-1,1-dione (Compound 18)

The compound prepared in Preparation 26 (10 mg, 15.5 $\mu$mol) was reacted with 1 equivalent of borontribromide according to the same procedure as Example 2 to give 5 mg (Yield 69%) of the title compound.

$^1$H NMR (DMSO-d$_6$, ppm); $\delta$11.0 (1H, s), 9.68 (1H, s), 8.45 (1H, s), 8.13 (1H, d), 7.87 (1H, s), 7.70 (1H, s), 7.11 (1H, d), 3.88 (2H, t), 3.50 (2H, t), 2.53 (2H, q), 2.49(3H, s)

FAB MS (m/e)=466[M$^+$+1]

Preparation 38

Synthesis of 2-(benzyloxy)-5-[3-(benzyloxy)-8-(1,1-dioxo-1$\lambda^6$-isothiazolidin-2-yl)-6-methyl-4-oxo-4H-chromen-2-yl]benzonitrile The compound prepared in Preparation 26 (164 mg, 253 $\mu$mol) was dissolved in dimethylformamide (20 ml), bis-tribenzylidenedipalladium (10 mg), diphenylphosphinoferrocene (20 mg) and zinc cyanide (ZnCN$_2$; 149 mg) were added thereto, and the resulting mixture was refluxed for 4 hours. After reaction, the solid was filtered out and the solvent was removed. The residue was dissolved again in ethylacetate (50 ml), washed with water (50 ml), and then concentrated. The residue was purified by silica gel column chromatography (eluent: 75% ethylacetate/hexane) to give 50 mg (Yield 33.4%) of the title compound.

$^1$H NMR (DMSO-d$_6$, ppm); $\delta$8.30 (1H, s), 8.24 (1H, d), 8.04 (1H, s), 7.60 (1H, s), 7.46–7.22 (10H, m), 7.01 (1H, d), 5.28 (2H, s), 5.11 (2H, s), 3.82 (2H, t), 3.39 (2H, t), 2.60 (2H, q), 2.47 (3H, s)

FAB MS (m/e)=592[M$^+$+1]

EXAMPLE 19

Synthesis of 5[-8-(1,1-dioxo-1$\lambda^6$-isothiazolidin-2-yl)-3-hydroxy-6-methyl-4-oxo-4H-chromen-2-yl]-2-hydroxybenzonitrile (Compound 19)

The compound prepared in Preparation 38 (10 mg, 16.9 $\mu$mol) was reacted according to the same procedure as Example 15 except that the reaction was carried out under hydrogen pressure of 1 atm to give 6 mg (Yield 86%) of the title compound.

$^1$H NMR (CDCl$_3$, ppm); $\delta$8.30 (1H, s), 8.07 (1H, d), 7.83 (1H, s), 7.63 (1H, s), 6.58 (1H, d), 3.87 (2H, t), 3.48 (2H, t), 2.55 (2H, q), 2.43 (3H, s)

FAB MS (m/e)=413[M$^+$+1]

Preparation 39

Synthesis of (E)-3-[2,4bis(benzyloxy)phenyl]-1-(2-hydroxy-5-methyl-3-nitrophenyl)-2-propen-1-one 2-Hydroxy-5-methyl-3-nitroacetophenone (500 mg, 2.56 mmol) and 2,4-dibenzyloxybenzaldehyde (900 mg, 2.83 mmol) were reacted according to the same procedure as Preparation 22 to give 540 mg (Yield 43%) of the title compound.

$^1$H NMR (CDCl$_3$, ppm); $\delta$8.10 (1H, d), 7.93 (1H, d), 7.72 (1H, d), 7.57–7.30 (13H, m), 5.13 (2H, s), 5.11 (2H, s), 2.22 (3H, s)

FAB MS (m/e)=496[M$^+$+1]

Preparation 40

Synthesis of 2-[2,4-bis(benzyloxy)phenyl]-3-hydroxy-6-methyl-8-nitro-4H-chromen-4-one The compound prepared in Preparation 39 (540 mg, 1.08 mmol) was reacted according to the same procedure as Preparation 23 to give 480 mg (Yield 87%) of the title compound.

$^1$H NMR (CDCl$_3$, ppm); $\delta$8.34 (1H, s), 8.14 (1H, s), 7.70–7.20 (11H, m), 6.73 (2H, m), 6.46 (1H, s), 5.12 (2H, s), 5.08 (2H, s), 2.53 (3H, s)

FAB MS (m/e)=510[M$^+$+1]

Preparation 41

Synthesis of 3-(benzyloxy)-2-[2,4-bis(benzyloxy)phenyl]-6-methyl-8-nitro-4H-chromen-4-one The compound prepared in Preparation 40 (480 mg, 0.94 mmol) was reacted according to the same procedure as Preparation 24 to give 436 mg (Yield 77%) of the title compound.

$^1$H NMR (CDCl$_3$, ppm); $\delta$8.39 (1H, s), 8.13 (1H, s), 7.60–7.13 (16H, m), 6.64 (2H, m), 5.14 (2H, s), 5.10 (2H, s), 5.00 (2H, s), 2.58 (3H, s)

FAB MS (m/e)=600[M$^+$+1]

Preparation 42

Synthesis of 8-amino-3-(benzyloxy)-2-[2,4-bis(benzyloxy)phenyl]-6-methyl-4H-chromen-4-one The compound prepared in Preparation 41 (100 mg, 166 $\mu$mol) was reacted according to the same procedure as Preparation 31 to give 85 mg (Yield 90%) of the title compound.

$^1$H NMR (CDCl$_3$, ppm); $\delta$7.45–7.08 (18H, m), 6.57 (2H, m), 5.10–4.92 (6H, m), 2.35 (3H, s)

FAB MS (m/e)=570[M$^+$+1]

Preparation 43

Synthesis of 2-{3-(benzyloxy)-2-[2,4-bis(benzyloxy)phenyl]-6-methyl-4-oxo-4H-chromen-8-yl}-1$\lambda^6$-isothiazolidin-1,1-dione The compound prepared in Preparation 42 (80 mg, 140 $\mu$mol) was reacted according to the same procedure as Preparation 26 to give 70 mg (Yield 74%) of the title compound.

$^1$H NMR (CDCl$_3$, ppm); $\delta$8.03 (1H, s), 7.60 (1H, s), 7.44–7.02 (16H, m), 6.62 (2H, m), 5.10 (2H, s), 5.04 (2H, s), 4.88 (2H, s), 3.55 (2H, t), 3.12 (2H, t), 2.49 (3H, s), 2.28 (2H, m)

FAB MS (m/e)=674[M$^+$+1]

EXAMPLE 20

Synthesis of 2-[2-(2,4-dihydroxyphenyl)-3-hydroxy-6-methyl-4-oxo-4H-chromen-8-yl]-1$\lambda^6$-isothiazolidin-1,1-dione (Compound 20)

The compound prepared in Preparation 43 (50 mg, 74 $\mu$mol) was reacted according to the same procedure as Example 15 except that the reaction was carried out under hydrogen pressure of 1 atm to give 26.2 mg (Yield 87%) of the title compound.

$^1$H NMR (DMSO-d$_6$, ppm); $\delta$9.76 (1H, br s), 7.86 (1H, s), 7.59 (1H, s), 7.34 (1H d), 6.38 (1H, s), 6.35 (1H, d), 3.87 (2H, m), 3.31 (2H, m), 2.43 (5H, m)

FAB MS (m/e)=404[M$^+$+1]

Preparation 44

Synthesis of (E)-3-(3-chloro-4-fluorophenyl)-1-(2-hydroxy-5-methyl-3-nitrophenyl)-2-propen-1-one 2-Hydroxy-5-methyl-3-nitroacetophenone (500 mg, 2.56 mmol) and 3-chloro-4-fluorobenzaldehyde (486 mg, 3.07 mmol) were reacted according to the same procedure as Preparation 22 to give 800 mg (Yield 94%) of the title compound.

$^1$H NMR (CDCl$_3$, ppm); $\delta$8.30–8.06 (41H, m), 7.23 (2H, m), 2.39 (3H, s)

FAB MS (m/e)=336[M$^+$+1]

Preparation 45

Synthesis of 2-(3-chloro-4-fluorophenyl)-3-hydroxy-6-methyl-8-nitro-4H-chromen-4-one The compound prepared in Preparation 44 (800 mg, 2.38 mmol) was reacted according to the same procedure as Preparation 23 to give 600 mg (Yield 72%) of the title compound.

$^1$H NMR (CDCl$_3$, ppm); $\delta$11.70 (1H, br s), 8.30–8.06 (4H, m), 7.23 (1H, m), 2.39 (3H, s)

FAB MS (m/e)=350[M$^+$+1]

Preparation 46
Synthesis of 2-(3-chloro-4-fluorophenyl)-3-methoxy-6-methyl-8-nitro-4H-chromen-4-one The compound prepared in Preparation 45 (810 mg, 2.3 mmol) was reacted according to the same procedure as Preparation 24 except that iodomethane was used instead of benzyl bromide to give 750 mg (Yield 89%) of the title compound.

$^1$H NMR (CDCl$_3$, ppm); δ8.32 (1H, m), 8.24 (1H, s), 8.18 (1H, s), 8.13(1H, m), 7.24 (1H, m), 3.87 (3H, s), 2.48 (3H, s)

FAB MS (m/e)=364[M$^+$+1]

Preparation 47
Synthesis of 8-amino-2-(3-chloro-4-fluorophenyl)-3-methoxy-methyl-4H-chromen-4-one The compound prepared in Preparation 46 (200 mg, 0.55 mmol) was reacted according to the same procedure as Example 15 except that dichloromethane was used as the solvent instead of 10% methanol/dichloromethane to give 130 mg (Yield 70%) of the title compound.

$^1$H NMR (CDCl$_3$, ppm); δ8.08 (1H, d), 7.95 (1H, m), 7.33 (1H, s), 7.25 (1H, m), 6.84 (1H, s), 3.81 (3H, s), 2.32 (3H, s)

FAB MS (m/e)=334[M$^+$+1]

Preparation 48
Synthesis of 2-[2-(3-chloro-4-fluorophenyl)-3-methoxy-6-methyl-4-oxo-4H-chromen-8-yl]-1λ$^6$-isothiazolidin-1,1-dione The compound prepared in Preparation 47(30 mg, 90 μmol) was reacted according to the same procedure as Preparation 26 to give 21 mg (Yield 53%) of the title compound.

$^1$H NMR (CDCl$_3$, ppm); δ8.29 (1H, s), 8.14 (1H, s), 8.03 (1H, s), 7.61 (1H, s), 7.25 (2H, m), 3.88 (3H, s), 3.84 (2H, m), 3.41 (2H, m), 2.63 (2H, m), 2.46 (3H, s)

FAB MS (m/e)=438[M$^+$+1]

EXAMPLE 21
Synthesis of 2-[2-(3-chloro-4-fluorophenyl)-3-hydroxy-6-methyl-4-oxo-4H-chromen-8-yl]-1λ$^6$-isothiazolidin-1,1-dione (Compound 21)

The compound prepared in Preparation 48 (21 mg, 48 μmol) was reacted according to the same procedure as Preparation 29 to give 16 mg (Yield 78%) of the title compound.

$^1$H NMR (CDCl$_3$, ppm); δ8.38 (1H, m), 8.24 (1H, m), 8.01 (1H, s), 7.66 (1H, s), 7.35–7.25 (2H, m), 3.89 (2H, t), 3.44 (2H, t), 2.67 (2H, m), 2.48 (3H, s)

FAB MS (m/e)=424[M$^+$+1]

Preparation 49
Synthesis of (E)3-[4-(benzyloxy)-3-methylphenyl]-1-(2-hydroxy-5-methyl-3-nitrophenyl)-2-propen-1-one 2-Hydroxy-5-methyl-3-nitroacetophenone (345 mg, 1.76 mmol) and 3-methyl-4-benzyloxybenzaldehyde (400 mg, 1.76 mmol) were reacted according to the same procedure as Preparation 22 to give 470 mg (Yield 66%) of the title compound.

$^1$H NMR (CDCl$_3$, ppm); δ8.01 (s, 1H), 7.93–7.86 (2H, m), 7.53–7.38 (10H, m), 6.93 (1H, d), 5.15 (2H, s), 2.42 (3H, s), 2.32 (3H, s)

FAB MS (m/e)=404[M$^+$+1]

Preparation 50
Synthesis of 2-[4-(benzyloxy)-3-methylphenyl]-3-hydroxy-6-methyl-8-nitro-4H-chromen-4-one The compound prepared in Preparation 49 (470 mg, 1.16 mmol) was reacted according to the same procedure as Preparation 23 to give 420 mg (Yield 83%) of the title compound.

$^1$H NMR (CDCl$_3$, ppm); δ8.33 (1H, s), 8.22 (3H, m), 7.46–7.33 (5H, m), 7.15 (1H, d), 6.90 (1H, s), 5.19 (2H, s), 2.56 (3H, s), 2.39 (3H, s)

FAB MS (m/e)=418[M$^+$+1]

Preparation 51
Synthesis of 3-(benzyloxy)-2-[4(benzyloxy)-3-methylphenyl]-6-methyl-8-nitro-4H-chromen-4-one The compound prepared in Preparation 50 (420 mg, 1.00 mmol) was reacted according to the same procedure as Preparation 24 to give 380 mg (Yield 74%) of the title compound.

$^1$H NMR (CDCl$_3$, ppm); δ8.35 (1H, s), 8.18 (1H, s), 8.10 (2H, m), 7.46–7.29 (9H, m), 6.95 (1H, d), 5.17 (2H, s), 5.15 (2H, s), 2.55 (3H, s), 2.29 (3H, s)

FAB MS (m/e)=508 [M$^+$+1]

Preparation 52
Synthesis of 8-amino-3-(benzyloxy)-2-[4(benzyloxy)-3-methylphenyl]-6-methyl-4H-chromen-4-one The compound prepared in Preparation 51 (380 mg, 749 μmol) was reacted according to the same procedure as Preparation 31 to give 330 mg (Yield 92%) of the title compound.

$^1$H NMR (CDCl$_3$, ppm); δ7.79 (2H, d), 7.45–7.30 (8H, m), 6.93 (1H, d), 6.83 (1H, s), 5.16 (2H, s), 5.08 (2H, s), 4.07 (2H, br s), 2.37 (3H, s), 2.29 (3H, s)

FAB MS (m/e)=478[M$^+$+1]

Preparation 53
Synthesis of 2-{3-(benzyloxy)-2-[4-(benzyloxy)-3-methylphenyl]-6-methyl-4-oxo-4H-chromen-8-yl}-1λ$^6$-isothiazolidin-1,1-dione The compound prepared in Preparation 52 (330 mg, 69 μmol) was reacted according to the same procedure as Preparation 26 to give 370 mg (Yield 92%) of the title compound.

$^1$H NMR (CDCl$_3$, ppm); δ8.05 (1H, s), 7.93 (2H, m), 7.65 (1H, s), 7.50–7.20 (7H, m), 6.95 (1H, d), 5.16 (2H, s), 5.05 (2H, s), 3.85 (2H, t), 3.38 (2H, t), 2.58 (2H, m), 2.47 (3H, s), 2.29 (3H, s)

FAB MS (m/e)=582[M$^+$+1]

EXAMPLE 22
Synthesis of 2-[3-hydroxy-2-(4-hydroxy-3-methylphenyl)-6-methyl-4oxo-4-chromen-8-yl]-1λ$^6$-isothiazolidin-1,1-dione (Compound 22)

The compound prepared in Preparation 53 (370 mg, 636 μmol) was reacted according to the same procedure as Example 15 to give 219 mg (Yield 85.7%) of the title compound.

$^1$H NMR (DMSO-d$_6$, ppm); δ10.50 (1H, br s), 9.40 (1H, br s), 8.04 (1H, s), 7.99 (1H, d), 7.86 (1H, s), 7.67 (1H, s), 6.94 (1H, d), 3.88 (2H, t), 3.50 (2H, t), 2.53 (2H, m), 2.44 (3H, s), 2.19 (3H, s)

FAB MS (m/e)=402 [M$^+$+1]

Preparation 54
Synthesis of (E)-3-{4-(allyloxy)-3-[(allyloxy)methyl]phenyl}-1-(2-hydroxy-5-methyl-3-nitrophenyl)-2-propen-1-one 2-Hydroxy-5-methyl-3-nitroacetophenone (500 mg, 2.56 mmol) and 4-(allyloxy)-3-[(allyloxy)methyl]benzaldehyde (760 mg, 3.27 mmol) were reacted according to the same procedure as Preparation 22 to give 470 mg (Yield 45%) of the title compound.

$^1$H NMR (CDCl$_3$, ppm); δ8.01 (1H, s), 7.94 (1H, s), 7.89 (1H, d), 7.81 (1H, s), 7.54 (1H, d), 7.48 (1H, d), 6.90 (1H, d), 6.02 (2H, m), 5.44–5.20 (4H, m), 4.62 (4H, s), 4.14 (2H, d), 2.42 (3H, s)

FAB MS (m/e)=410[M$^+$+1]

Preparation 55

Synthesis of 2-{4-(allyloxy)-3-[(allyloxy)methyl]phenyl}-3-hydroxy-6-methyl-8-nitro-4H-chromen-4-one The compound prepared in Preparation 54 (470 mg, 1.15 mmol) was reacted according to the same procedure as Preparation 23 to give 296 mg (Yield 61%) of the title compound.

$^1$H NMR (CDCl$_3$, ppm); δ8.50 (1H, s), 8.33 (1H, s), 8.30 (1H, d), 8.24 (1H, s), 7.02 (1H, d), 6.91 (1H, br s), 6.04 (2H, m), 5.46–5.20 (4H, m), 4.66 (4H, m), 4.16 (2H, d), 2.56 (3H, s)

FAB MS (m/e)=424[M$^+$+1]

Preparation 56

Synthesis of 3-(allyloxy)-2-{4-(allyloxy)-3-[(allyloxy)methyl]phenyl}-6-methyl-8-nitro-4H-chromen-4one The compound prepared in Preparation 55 (296 mg, 0.699 mmol) was reacted according to the same procedure as Preparation 24 except that allylbromide was used instead of benzylbromide to give 259 mg (Yield 80%) of the title compound.

$^1$H NMR (CDCl$_3$, ppm); δ8.45 (1H, s), 8.32 (1H, s), 8.25 (1H, d), 8.19 (1H, s), 6.99 (1H, d), 6.02 (3H, m), 5.50–5.15 (6H, m), 4.66 (6H, m), 4.15 (2H, d), 2.54 (3H, s)

FAB MS (m/e)=464 [M$^+$+1]

Preparation 57

Synthesis of 3-(allyloxy)-2-{4-(allyloxy)-3-[(allyloxy)methyl]phenyl}-8-amino-6-methyl-4H-chromen-4one The compound prepared in Preparation 56 (259 mg, 0.559 mmol) was reacted according to the same procedure as Preparation 31 to give 150 mg (Yield 61%) of the title compound.

$^1$H NMR (CDCl$_3$, ppm); δ8.13 (1H, s), 8.04 (1H, d), 7.39 (1H, s), 6.95 (1H, d), 6.82 (1H, s), 6.07–5.90 (3H, m), 5.50–5.10 (6H, m), 4.76–4.60 (6H, m), 4.13 (2H, d), 2.36 (3H, s)

FAB MS (m/e)=434[M$^+$+1]

Preparation 58

Synthesis of 2-(3-(allyloxy)-2-{4-(allyloxy)-3-[(allyloxy)methyl]phenyl}-6-methyl-4-oxo-4H-chromen-8-yl)-1λ$^6$-isothiazolidin-1,1-dione The compound prepared in Preparation 57 (150 mg, 346 μmol) was reacted according to the same procedure as Preparation 26 to give 111 mg (Yield 59%) of the title compound.

$^1$H NMR (CDCl$_3$, ppm); δ8.19 (2H, s), 8.00 (1H, s), 7.66 (1H, d), 6.95 (1H, d), 6.08–6.00 (3H, m), 5.45–5.10 (6H, m), 4.64–4.59 (6H, m), 4.13 (2H, s), 3.86 (2H, t), 3.39 (2H, t), 2.60 (2H, m), 2.44 (3H, s)

FAB MS (m/e)=538 [M$^+$+1]

EXAMPLE 23

Synthesis of 2-{3-hydroxy-2-[4-hydroxy-3-(hydroxymethyl)phenyl]-6-methyl-4-oxo-4H-chromen-8-yl}-1λ$^6$-isothiazolidin-1,1-dione (Compound 23)

The compound prepared in Preparation 58 (10 mg, 18.6 μmol) was dissolved in 90% aqueous methanol solution, catalytic amount of p-toluenesulfonic acid and catalytic amount of 10% Pd/C were added thereto, and the resulting mixture was refluxed for 6 hours. The reaction mixture was filtered through a cellite and then concentrated. The residue was purified by silica gel column chromatography (eluent: 10% methanol/methylene chloride) to give 2.4 mg (Yield 30%) of the title compound.

$^1$H NMR (CD$_3$OD+CDCl$_3$, ppm); δ8.04 (1H, s), 8.02 (1H, d), 7.83 (1H, s), 7.52 (1H, s), 6.82 (1H, d), 4.67 (2H, s), 3.81 (2H, t), 3.36 (2H, t), 2.56 (2H, m), 2.34 (3H, s)

FAB MS (m/e)=418[M$^+$+1]

Preparation 59

Synthesis of 2-{3(benzyloxy)-2-[4-(benzyloxy)-3-(trifluoromethyl)phenyl]-6-methyl-4oxo-4H-chromen-8-yl}-1λ$^6$-isothiazolidin-1,1-dione The compound prepared in Preparation 26 (100 mg, 155 μmol) was dissolved in dimethylformamide (5 ml), 2 equivalents of fluorosulfonyl(difluoromethyl)acetic acid methylester and catalytic amount of cuprous iodide (CuI) were added thereto, and the resulting mixture was reacted for 10 hours at 80° C. Water and ethylacetate were added and the mixture thus obtained was stirred. The organic layer was separated, filtered through a silica gel pad, and then concentrated to give 75 mg (Yield 76%) of the title compound.

$^1$H NMR (DMSO-d$_6$, ppm); δ8.20 (1H, s), 8.10 (1H, d), 7.90 (1H, s), 7.73 (1H, s), 7.51–7.30 (1H, m), 5.32 (2H, s), 5.10 (2H, s), 3.86 (2H, t), 3.47 (2H, t), 2.50 (2H, m), 2.46 (3H, s)

FAB MS (m/e)=636[M$^+$+1]

EXAMPLE 24

Synthesis of 2-[3-hydroxy-2-(4-hydroxy-3-(trifluoromethyl)phenyl)-6-methyl-4-oxo-4H-chromen-8-yl]-1λ$^6$-isothiazolidin-1,1-dione (Compound 24)

The compound prepared in Preparation 59 (30 mg, 47 μmol) was reacted according to the same procedure as Example 15 to give 19.7 mg (Yield 91%) of the title compound.

$^1$H NMR (DMSO-d$_6$, ppm); δ8.30 (1H, s), 8.08 (1H, d), 7.86 (1H, s), 7.67 (1H, s), 7.11 (1H, d), 3.88 (2H, t), 3.49 (2H, t), 2.54 (2H, m), 2.45 (3H, s)

FAB MS (m/e)=456[M$^+$+1]

Preparation 60

Synthesis of N-(4-methoxyphenyl)acetamide

Paraanisidine (136.34 g, 1.108 mol) was dissolved in dichloromethane (500 ml), triethylamine (234 ml, 1.66 mol) and acetic anhydride (114.8 ml, 1.22 mol) were added thereto, and the resulting mixture was stirred for 1 hour. After completion of reaction, the reaction solution was concentrated. Water (800 ml) was added to the residue and the resulting mixture was stirred and filtered to give 168.0 g (1.16 mol, Yield 92%) of the title compound.

$^1$H NMR (CDCl$_3$, ppm); δ7.37 (2H, d), 6.84 (2H, d), 3.78 (3H, s), 2.14 (3H, s)

FAB MS (m/e)=166[M$^+$+1]

Preparation 61

Synthesis of N-(3-acetyl-4-hydroxyphenyl)acetamide

The compound prepared in Preparation 60 (167.44 g, 1.014 mol) and aluminum chloride (500 g, 3.76 mol) were mixed together in solid state, carbon disulfide (1340 ml) and acetylchloride (194 ml, 2.72 mol) were added thereto, and the resulting mixture was stirred for 3 hours. After completion of reaction, water (800 ml) of 0° C. was added over about 30 minutes. The mixture thus obtained was extracted with dichloromethane (800 ml) and then extracted with 1N aqueous sodium hydroxide solution (700 ml). The aqueous layer was neutralized by 1N aqueous hydrochloric acid solution to give a solid having a yellow color. This solid was filtered and dried to give 130.6 g (0.674 mol, Yield 67%) of the title compound.

$^1$H NMR (CDCl$_3$, ppm); δ12.10 (1H, s), 8.16 (1H, d), 7.31 (1H, dd), 7.17 (1H, s), 6.93 (1H, s), 2.62 (3H, s), 2.18 (3H, s)

FAB MS (m/e)=194[M$^+$+1]

Preparation 62

Synthesis of N-(3-acetyl-4-hydroxy-5-nitrophenyl)acetamide

To the compound prepared in Preparation 61 (120 g, 0.62 mol) was added acetic anhydride (1000 ml) and the mixture was cooled to 0° C. Dinitrocupper (107.2 g, 0.442 mol) was added thereto while a temperature of 0° C. was maintained and the resulting mixture was stirred for 2 hours. After completion of reaction, water (1L) of 0° C. was added and the resulting mixture was filtered and dried to give 90.4 g (0.378 mol, Yield 61%) of the title compound.

$^1$H NMR (DMSO-D$_6$, ppm); δ10.29 (1H, s), 8.53 (1H, s), 8.27 (1H, s), 2.66 (3H, s), 2.06 (3H, s)

FAB MS (m/e)=239[M$^+$+1]

Preparation 63

Synthesis of N-(3-{((E)-3-[4-(benzyloxy)phenyl]-2-propenoyl}-4-hydroxy-5-nitrophenyl)acetamide The compound prepared in Preparation 62 (32.3 g, 0.135 mol) was dissolved in 80% aqueous ethanol solution (600 ml), sodium hydroxide (16.3 g, 0.406 mol) and 4-benzyloxybenzaldehyde (34.5 g, 0.163 mol) were added thereto, and the resulting mixture was stirred for 24 hours. After completion of reaction, the reaction solution was neutralized by 1N aqueous hydrochloric acid solution. The yellow solid thus obtained was filtered, washed with water (300 ml) and methanol (200 ml), and then dried to give 53.2 g (0.123 mol, Yield 91%) of the title compound.

$^1$H NMR (DMSO-D$_6$, ppm); δ10.23 (1H, s), 8.54 (1H, s), 8.24 (1H, s), 7.81–7.11 (12H, m), 5.20 (2H, s), 2.06 (3H, s)

FAB MS (m/e)=433[M$^+$+1]

Preparation 64

Synthesis of N-{2-[4-(benzyloxy)phenyl]-3-hydroxy-8-nitro-4-oxo-4H-chromen-6-yl}acetamide The compound prepared in Preparation 63 (45 g, 0.104 mol) was mixed with methanol (500 ml), 10% aqueous sodium hydroxide solution (104 ml, 0.260 mol) and 30% aqueous hydrogen peroxide (50 ml, 0.441 mol) were added thereto, and the resulting mixture was stirred for 20 hours at room temperature. After completion of reaction, the reaction solution was neutralized by 1N aqueous hydrochloric acid solution. The yellow solid thus obtained was filtered, washed with water (300 ml) and methanol (200 ml), and then dried to give 24.3 g (54.4 mmol, Yield 52%) of the title compound.

$^1$H NMR (DMSO-D$_6$, ppm); δ10.58 (1H, s), 8.78 (1H, s), 8.64 (1H, s), 8.25 (2H, d), 7.49–7.37 (6H, m), 7.24 (2H, d), 5.21 (2H, s), 2.11 (3H, s)

FAB MS (m/e)=447[M$^+$+1]

Preparation 65

Synthesis of N-{3-(benzyloxy)-2-[4-(benzyloxy)phenyl]-8-nitro-4oxo-4H-chromen-6yl}acetamide The compound prepared in Preparation 64 (23 g, 51.5 mmol) was dissolved in N,N-dimethylformamide (300 ml), potassium carbonate (10.7 g, 77.3 mmol) and benzyl bromide (7.35 ml, 61.8 mmol) were added thereto, and the resulting mixture was stirred for 2 hours at room temperature. After completion of reaction, the reaction solution was concentrated. To the residue were added water (400 ml) and methanol (100 ml), which was then stirred for 30 minutes, filtered, washed with water (200 ml) and methanol (100 ml), and dried to give 26.8 g (50.0 mmol, Yield 97%) of the title compound.

1H NMR (DMSO-D$_6$, ppm); δ8.80 (1H, s), 8.61 (1H, s), 8.10 (2H, d), 7.46–7.31 (1H, m), 7.20 (2H, d), 5.20 (2H, s), 5.10 (2H, s), 2.12 (3H, s)

FAB MS (m/e)=537[M$^+$+1]

Preparation 66

Synthesis of N-{8-amino-3-(benzyloxy)-2-[4-(benzyloxy)phenyl]-4-oxo-4-chromen-6-yl}acetamide The compound prepared in Preparation 65 (25.0 g, 46.6 mmol) was dissolved in dichloromethane (400 ml) and ethanol (350 ml), iron (26 g, 466 mmol) and conc. hydrochloric acid (10 ml) were added thereto, and the resulting mixture was stirred under reflux for 7 hours. After completion of reaction, iron was filtered out and the filtrate was washed with dichloromethane (500 ml) and concentrated. Methanol (200 ml) was added to the residue and the resulting mixture was stirred and filtered to give 17.3 g (34.1 mmol, Yield 73%) of the title compound.

$^1$H NMR (DMSO-D$_6$, ppm); δ8.12 (2H, d), 7.48–7.29 (12H, m), 7.13 (2H, d), 5.22 (2H, s), 5.04 (2H, s), 2.05 (3H, s)

FAB MS (m/e)=507[M$^+$+1]

Preparation 67

Synthesis of N-{3-(benzyloxy)-2-[4-(benzyloxy)phenyl]-8-(1,1-dioxo-1λ$^6$-isothiazolidin-2-yl)-4-oxo-4H-chromen-6-yl}acetamide The compound prepared in Preparation 66 (16 g, 31.6 mmol) was dissolved in dichloromethane (300 ml), triethylamine (22 mg, 158 mmol), 3-chloropropanesulfonylchloride (28 g, 158 mmol) and N,N-dimethylaminopyridine (100 mg, 0.81 mmol) were added thereto, and the resulting mixture was stirred for 1 hour at room temperature. After reaction was completed, the reaction solution was concentrated. To the residue were added N,N-dimethylformamide (300 ml) and 2N aqueous sodium hydroxide solution (200 ml, 400 mmol) and the resulting mixture was stirred for 2 hours while heated to about 60° C. After completion of reaction, water (400 ml) was added and stirred at room temperature. The yellow solid thus obtained was filtered, washed with methanol (200 ml), and then dried to give 18.3 g (30 mmol, Yield 95%) of the title compound.

$^1$H NMR (CDCl$_3$, ppm); δ8.50 (1H, s), 8.08 (2H, d), 8.01 (1H, s), 7.46–7.23 (10H, m), 7.02 (2H, d), 5.13 (2H, d), 5.01 (2H, d), 3.88 (2H, t), 3.33 (2H, t), 2.59 (2H, quin), 2.97 (3H, s)

FAB MS (m/e)=611[M$^+$+1]

Preparation 68

Synthesis of 2-{6-amino-3-(benzyloxy)-2-[4-(benzyloxy)phenyl]-4-oxo-4H-chromen-8-yl}-1λ$^6$-isothiazolidin-1,1-dione The compound prepared in Preparation 67 (15 g, 24.6 mmol) was dissolved in dichloromethane (200 ml) and methanol (200 ml), 2N aqueous sodium hydroxide solution (100 ml) was added thereto, and the resulting mixture was stirred under reflux for 1 hour. After completion of reaction, the reaction solution was concentrated. To the residue was added water (200 ml), which was then neutralized by 1N aqueous hydrochloric acid solution. The yellow solid thus obtained was filtered, washed with water (200 ml) and methanol (100 ml), and then dried to give 13.2 g (23.2 mmol, Yield 94%) of the title compound.

$^1$H NMR (CDCl$_3$, ppm); δ7.98 (2H, d), 7.45–7.20 (10H, m), 7.02 (2H, d), 5.13 (2H, s), 5.02 (2H, s), 3.90 (2H, s), 3.83 (2H, t), 3.37 (2H, t), 2.55 (2H, quin)

FAB MS (m/e)=569[M$^+$+1]

Preparation 69

Synthesis of 2-{6-anilino-3-(benzyloxy)2-[4-(benzyloxy)phenyl]-1λ$^6$isothiazolidin-1,1-dione The compound prepared in Preparation 68 (110 mg, 0.193 mmol), iodobenzene (197 mg, 0.967 mmol), sodium tert-butoxide (93 mg, 0.967 mmol), palladium dibenzylideneacetone (35 mg, 0.039 mmol) and binap (30 mg, 0.039 mmol) were mixed, toluene (20 ml) was added thereto, and the resulting mixture was stirred under reflux for 2 hours. After completion of reaction, the solid was filtered out and the filtrate was washed with water (30 ml×2). The resulting solution was concentrated and the residue was purified by column chromatography (eluent: ethylacetate/n-hexane=1/1, v/v) to give 78 mg (0.12 mmol, Yield 63%) of the title compound;

$^1$H NMR (CDCl$_3$, ppm); δ8.01 (2H, d), 7.82 (1H, d), 7.52 (1H, d), 7.45–7.24 (12H, m), 7.15 (2H, d), 7.04–7.02 (3H, m), 5.93 (1H, s), 5.14 (2H, s), 5.03 (2H, s), 3.85 (2H, t), 3.37 (2H, t), 2.56 (2H, quin)

FAB MS (m/e)=645[M$^+$+1]

Preparation 70

Synthesis of t-butyl acetyl [3-(benzyloxy)-2-[4-(benzyloxy) phenyl]-8-(1,1-dioxo-1λ$^6$-isothiazolidin-2-yl)-4oxo-4H-chromen-6-yl]carbamate The compound prepared in Preparation 67 (1.0 g, 1.64 mmol) was dissolved in dichloromethane (70 ml), di-t-butoxydicarbonyl (394 mg, 1.84 mmol) and N,N-dimethyl-aminopyridine (30 mg, 0.245 mmol) were added thereto, and the resulting mixture was stirred for 2 hours at room temperature. After completion of reaction, the reaction solution was concentrated. To the residue was added water (80 ml), which was then stirred, filtered, washed with methanol (20 ml) and dried to give 1.13 g (1.58 mmol, Yield 97%) of the title compound.

$^1$H NMR (CDCl$_3$, ppm); δ8.02 (2H, d), 7.99 (1H, s), 7.56 (1H, s), 7.47–7.26 (10H, m), 7.04 (2H, d), 5.14 (2H, s), 5.06 (2H, s), 3.86 (2H, t), 3.37 (2H, t), 2.65 (3H, s), 2.57 (2H, quin), 1.49 (9H, s)

FAB MS (m/e)=711[M$^+$+1]

Preparation 71

Synthesis of t-butyl 3-(benzyloxy)-2-[4-(benzyloxy) phenyl]-8-(1,1-dioxo-1λ$^6$-isothiazolidin-2-yl)-4-oxo-4H-chromen-6-ylcarbamate The compound prepared in Preparation 70 (1.10 g, 1.55 mmol) was dissolved in dichloromethane (70 ml) and methanol (70 ml), 2N aqueous sodium hydroxide solution (40 m, 80 mmol) was added thereto, and the resulting mixture was stirred under reflux for 1 hour. After completion of reaction, the reaction solution was concentrated. To the residue was added water (100 ml), which was then neutralized by 1N aqueous hydrochloric acid solution, filtered, washed with water (50 ml) and methanol (20 ml) and dried to give 950 mg (1.42 mmol, Yield 92%) of the title compound.

$^1$H NMR (CDCl$_3$, ppm); δ8.07 (1H, s), 8.05 (2H, d), 8.01 (1H, s), 7.88 (1H, s), 7.45–7.26 (10H, m), 7.03 (2H, d), 5.13 (2H, s), 5.02 (2H, s), 3.87 (2H, t), 3.37 (2H, t), 2.57 (2H, quin), 1.51 (9H, s)

FAB MS (m/e)=669[M$^+$+1]

Preparation 72

Synthesis of t-butyl 3-(benzyloxy)-2-[4-(benzyloxy) phenyl]-8-(1,1-dioxo-1λ$^6$-isothiazolidin-2-yl)-4-oxo-4H-chromen-6-yl(methyl)carbamate The compound prepared in Preparation 71 (450 mg, 0.67 mmol) was dissolved in tetrahydrofuran (50 ml), sodium hydride (54 mg, 60%, 1.34 mmol) and iodomethane (3 ml, 48.2 mmol) were added thereto, and the resulting mixture was stirred for 1 hour at room temperature. After completion of reaction, methanol (10 ml) was added to the reaction solution and concentrated. To the residue was added water (50 ml), which was then stirred, filtered and dried to give 440 mg (0.64 mmol, Yield 96%) of the title compound.

$^1$H NMR (CDCl$_3$, ppm); δ8.03 (2H, d), 7.45–7.26 (12H, m), 7.04 (2H, d), 5.14 (2H, s), 5.04 (2H, s), 3.86 (2H, t), 3.37 (2H, t), 3.34 (3H, s), 2.57 (2H, quin), 1.50 (9H, s)

FAB MS (m/e)=683[M$^+$+1]

Preparation 73

Synthesis of 2-[3-(benzyloxy)-2-[4-(benzyloxy)phenyl]-6-(methylamino)-4-oxo-4H-chromen-8-yl]-1λ$^6$-isothiazolidin-1,1-dione To the compound prepared in Preparation 72 (200 mg, 0.29 mmol) were added dichloromethane (15 ml) and trifluoroacetic acid (8 ml), and the resulting mixture was stirred for 1 hour at room temperature. After reaction was completed, the reaction solution was concentrated. To the residue was added diethylether (40 ml), and the resulting mixture was stirred, filtered, washed with methanol (20 ml) and dried to give 155 mg (0.266 mmol, Yield 92%) of the title compound.

$^1$H NMR (CDCl$_3$, ppm); δ8.02 (2H, d), 7.46–7.26 (12H, m), 7.02 (2H, d), 5.13 (2H, s), 5.05 (2H, s), 3.86 (2H, t), 3.37 (2H, t), 3.34 (3H, s), 2.57 (2H, quin)

FAB MS (m/e)=583[M$^+$+1]

Preparation 74

Synthesis of 2-{3-(benzyloxy)-6-{[2-(benzyloxy)ethyl]amino}-2-[4-(benzyloxy)phenyl-4-oxo-4H-chromen-8-yl)}-1λ$^6$-isothiazolidin-1,1-dione The compound prepared in Preparation 68 (54 mg, 0.094 mmol) was dissolved in dichloromethane (15 ml), benzyloxyacetaldehyde (47 mg, 0.32 mmol) and sodium triacetoxyborohydride (64 mg, 0.30 mmol) were added thereto, and the resulting mixture was stirred for 1 hour at room temperature. After completion of reaction, the reaction solution was washed with water (20 ml×2) and concentrated. The residue was purified by column chromatography (eluent: ethylacetate/n-hexane=1/1, v/v) to give 59 mg (0.084 mmol, Yield 89%) of the title compound.

$^1$H NMR (CDCl$_3$, ppm); δ8.00 (2H, d), 7.46–7.24 (16H, m), 7.13 (1H, s), 7.02 (2H, d), 5.13 (2H, s), 5.03 (2H, s), 4.56 (2H, s), 4.33 (1H, t), 3.80 (2H, t), 3.74 (2H, t), 3.40 (2H, t), 3.36 (2H, t), 2.54 (2H, quin)

FAB MS (m/e)=703[M$^+$+1]

Preparation 75

Synthesis of 3-chloro-4-hydroxybenzaldehyde

Acetic acid (300 ml) was bubbled with chlorine gas to make 38.38 g (0.541 mol) of chlorine. 4-Hydroxybenzaldehyde (66.1 g, 0.541 mol) was dissolved in acetic acid (300 ml) and stirred, during which the acetic acid solution containing chlorine as prepared above was slowly added thereto over 2 hours. The resulting mixture was stirred for further 2 hours. After completion of reaction, the reaction solution was concentrated. To the residue was added water (1L), which was then filtered, washed with water (500 ml) and dried to give 63.16 g (0.403 mol, Yield 75%) of the title compound.

$^1$H NMR (CDCl$_3$, ppm); 9.84 (1H, s), 7.89 (1H, s), 7.74 (1H, d), 7.15 (1H, d), 6.17 (1H, s)

FAB MS (m/e)=157[M$^+$+1]

Preparation 76

Synthesis of 4-(benzyloxy)-3-chlorobenzaldehyde

The compound prepared in Preparation 75 (63.16 g, 0403 mol) was dissolved in N,N-dimethylformamide (300 ml), potassium carbonate (72.4 g, 0.524 mol) and benzyl bromide (53 ml, 0.443 mol) were added thereto, and the resulting mixture was stirred for 4 hours at room temperature. After completion of reaction, the reaction solution was concentrated. To the residue was added water (500 ml), which was then filtered, washed with water (200 ml) and n-hexane (100 ml), and dried to give 88.56 g (0.359 mol, Yield 89%) of the title compound.

$^1$H NMR (CDCl$_3$, ppm); δ9.84 (1H, s), 7.93 (1H, s), 7.71 (1H, d), 7.46–7.32 (5H, m), 7.07 (1H, d), 5.26 (3H, s)

FAB MS (m/e)=247[M$^+$+1]

Preparation 77
Synthesis of N-(3-{(E)-3-[4-(benzyloxy)-3-chlorophenyl]-2-propenyl}-4-hydroxy-5-nitrophenyl)acetamide The compound prepared in Preparation 62 (30.0 g, 0.126 mol) was dissolved in 80% aqueous ethanol solution (600 ml), sodium hydroxide (16.3 g, 0.406 mol) and the compound prepared in Preparation 76 (38.5 g, 0.156 mol) were added thereto, and the resulting mixture was stirred for 24 hours. After completion of reaction, the reaction solution was neutralized by 1N aqueous hydrochloric acid solution. The yellow solid thus obtained was filtered, washed with water (400 ml) and methanol (200 ml), and dried to give 52.2 g (0.112 mol, Yield 89%) of the title compound.

$^1$H NMR (DMSO-D$_6$, ppm); δ12.23 (1H, s), 10.24 (1H, s), 8.52 (1H, s), 8.21 (1H, s), 8.05 (1H, s), 7.79–7.34 (9H, m), 5.30 (2H, s), 2.08 (3H, s)

FAB MS (m/e)=467[M$^+$+1]

Preparation 78
Synthesis of N-{2-[4-(benzyloxy)-3-chlorophenyl]-3-hydroxy-8-nitro-4-oxo-4H-chromen-6-yl}acetamide The compound prepared in Preparation 77 (50 g, 0.107 mol) was mixed with methanol (600 ml), 10% aqueous sodium hydroxide solution (104 ml, 0.260 mol) and 30% aqueous hydrogen peroxide (50 ml, 0.441 mol) were added thereto, and the resulting mixture was stirred for 20 hours at room temperature. After reaction was completed, the reaction solution was neutralized by 1N aqueous hydrochloric acid solution. The yellow solid thus obtained was filtered, washed with water (350 ml) and methanol (250 ml), and dried to give 26.2 g (54.5 mmol, Yield 51%) of the title compound.

$^1$H NMR (DMSO-D$_6$, ppm); δ10.56 (1H, s), 8.78 (1H, s), 8.64 (1H, s), 8.23 (1H, s), 7.92 (1H, d), 7.49–7.37 (6H, m), 7.22 (1H, d), 5.23 (2H, s), 2.10 (3H, s)

FAB MS (m/e)=481[M$^+$+1]

Preparation 79
Synthesis of N-{3-(benzyloxy)-2-[4-(benzyloxy)-3-chlorophenyl]-8-nitro-4-oxo-4H-chromen-6-yl}acetamide The compound prepared in Preparation 78 (24 g, 49.9 mmol) was dissolved in dimethylformamide (300 ml), potassium carbonate (10.7 g, 77.3 mmol) and benzylbromide (7.35 ml, 61.8 mmol) were added thereto, and the resulting mixture was stirred for 2 hours at room temperature. After completion of reaction, the reaction solution was concentrated. To the residue were added water (400 ml) and methanol (100 ml), and then the mixture thus obtained was stirred for 30 minutes, filtered, washed with water (200 ml) and methanol (100 ml), and dried to give 27.3 g (47.8 mmol, Yield 96%) of the title compound.

$^1$H NMR (DMSO-D$_6$, ppm); δ10.56 (1H, s), 8.78 (1H, s), 8.64 (1H, s), 8.23 (1H, s), 7.92 (1H, d), 7.49–7.29 (10H, m), 7.22 (1H, d), 5.23 (2H, s), 5.10 (2H, s), 2.10 (3H, s)

FAB MS (m/e)=571[M$^+$+1]

Preparation 80
Synthesis of N-{8-amino-3-(benzyloxy)-2-[4-(benzyloxy)-3-chlorophenyl]-4-oxo-4H-chromen-6-yl}acetamide The compound prepared in Preparation 79 (26.0 g, 45.5 mmol) was dissolved in dichloromethane (400 ml) and ethanol (350 ml), iron (26 g, 466 mmol) and conc. hydrochloric acid (10 ml) were added thereto, and the resulting mixture was stirred under reflux for 6 hours. After completion of reaction, iron was filtered out, and then the filtrate was washed with dichloromethane (500 ml) and concentrated. To the residue was added methanol (200 ml), which was then stirred and filtered to give 18.3 g (33.8 mmol, Yield 74%) of the title compound.

$^1$H NMR (DMSO-D$_6$, ppm); δ10.03 (1H, s), 8.20 (1H, s), 8.08 (1H, d), 7.45–7.29 (13H, s), 5.82 (2H, s), 5.34 (2H, s), 5.07 (2H, s), 2.05 (3H, s)

FAB MS (m/e)=541[M$^+$+1]

Preparation 81
Synthesis of N-{3-(benzyloxy)-2-[4-(benzyloxy)-3-chlorophenyl]-8-(1,1-dioxo-1λ$^6$-isothiazolidin-2-yl)-4-oxo-4H-chromen-6-yl}acetamide The compound prepared in Preparation 80 (17 g, 31.4 mmol) was dissolved in dichloromethane (300 ml), triethylamine (22 ml, 158 mmol), 3-chloropropanesulfonylchloride (28 g, 158 mmol) and N,N-dimethylaminopyridine (100 mg, 0.81 mmol) were added thereto, and the resulting mixture was stirred for 1 hour at room temperature. After reaction was completed, and reaction solution was concentrated. To the residue were added N,N-dimethylformamide (300 ml) and 2N aqueous sodium hydroxide solution (200 ml, 400 mmol), which was then stirred for 2 hours while heated to about 60° C. After completion of reaction, water (400 ml) was added and the resulting solution was stirred at room temperature. The yellow solid thus obtained was filtered, washed with methanol (200 ml), and dried to give 18.7 g (29.0 mmol, Yield 92%) of the title compound.

$^1$H NMR (CDCl$_3$, ppm); δ8.53 (1H, s), 8.22 (1H, s), 8.07 (1H, s), 8.01 (1H, d), 7.48–7.24 (10H, m), 7.00 (1H, d), 5.22 (2H, s), 5.04 (2H, s), 3.89 (2H, t), 3.38 (2H, t), 2.61 (2H, quin), 2.17 (3H, s)

FAB MS (m/e)=645[M$^+$+1]

Preparation 82
Synthesis of 2-{6-amino-3-(benzyloxy)-2-[4-(benzyloxy)-3-chlorophenyl]-4-oxo-4H-chromen-8-yl}-1λ$^6$-isothiazolidin-1,1-dione The compound prepared in Preparation 81 (12 g, 18.6 mmol) was dissolved in dichloromethane (150 ml) and methanol (150 ml), 2N aqueous sodium hydroxide solution (100 ml) was added thereto, and the resulting mixture was stirred under reflux for 1 hour. After reaction was completed, the reaction solution was concentrated. To the residue was added water (200 ml), which was then neutralized by 1N aqueous hydrochloric acid solution. The yellow solid thus obtained was filtered, washed with water (200 ml) and methanol (100 ml), and dried to give 10.4 g (17.2 mmol, Yield 93%) of the title compound.

$^1$H NMR (CDCl$_3$, ppm); δ8.10 (1H, s), 7.96 (1H, d), 7.48–7.19 (12H, m), 6.99 (1H, d), 5.23 (2H, s), 5.06 (2H, s), 3.91 (2H, s), 3.81 (2H, t), 3.38 (2H, t), 2.58 (2H, quin)

FAB MS (m/e)=603[M$^+$+1]

Preparation 83
Synthesis of 2-{3-(benzyloxy)-2-[4-(benzyloxy)-3-chlorophenyl]-6-(dimethylamino)4-oxo-4H-chromen-8-yl}-1λ$^6$-isothiazolidin-1,1-dione The compound prepared in Preparation 82 (500 mg, 0.829 mmol) was dissolved in acetone (70 ml), potassium carbonate (300 mg, 2.17 mmol) and iodomethane (5 ml, 80.3 mmol) were added thereto, and the resulting mixture was stirred under reflux for 3 hours. After completion of reaction, the reaction solution was concentrated. To the residue was added water (50 ml), which was then stirred, filtered, and dried to give 495 mg (0.784 mmol, Yield 95%) of the title compound.

$^1$H NMR (DMSO-D$_6$, ppm); δ8.19 (1H, s), 8.04 (1H, d), 7.48–7.30 (12H, m), 6.99 (1H, d), 5.32 (2H, s), 5.06 (2H, s), 3.88 (2H, t), 3.39 (2H, t), 3.01 (6H, s), 2.58 (2H, quin)

FAB MS (m/e)=631[M$^+$+1]

Preparation 84
Synthesis of t-butyl acetyl [3-(benzyloxy)-2-[4-(benzyloxy)-3-chlorophenyl]-8-(1,1-dioxo-1λ$^6$-isothiazolidin-2-yl)-4-oxo-4H-chromen-6-yl]carbamate The compound prepared in Preparation 81 (1.05 g, 1.63 mmol) was dissolved in dichloromethane (70 ml), di-t- butyloxydicarbonyl (394 mg, 1.84 mmol) and N,N-dimethyl-aminopyridine (30 mg, 0.245 mmol) were added thereto, and the resulting mixture was stirred for 2 hours at room temperature. After completion of reaction, the reaction solution was concentrated. To the residue was added water (80 ml), which was then stirred, filtered, washed with methanol (20 ml), and dried to give 1.15 g (1.54 mmol, Yield 95%) of the title compound.

$^1$H NMR (CDCl$_3$, ppm); δ8.12 (1H, s), 7.98–7.96 (2H, m), 7.58(1H, s), 7.48–7.24 (10H, m), 7.00 (1H, d), 5.24 (2H, s), 5.11 (2H, s), 3.85 (2H, t), 3.39 (2H, t), 2.65 (3H, s), 2.60 (2H, quin), 1.40 (9H, s)

FAB MS (m/e)=745[M$^+$+1]

Preparation 85

Synthesis of t-butyl 3-(benzyloxy)-2-[4-(benzyloxy)-3-chlorophenyl]-8-(1,1-dioxo-1λ$^6$-isothiazolidin-2-yl)-4-oxo-4-chromen-6-ylcarbamate The compound prepared in Preparation 84 (1.10 g, 1.48 mmol) was dissolved in dichloromethane (70 ml) and methanol (70 ml), 2N aqueous sodium hydroxide solution (40 ml, 80 mmol) was added thereto, and the resulting mixture was stirred under reflux for 1 hour. After completion of reaction, the reaction solution was concentrated. To the residue was added water (100 ml), which was then neutralized by 1N aqueous hydrochloric acid solution, filtered, washed with water (50 ml) and methanol (20 ml), and dried to give 980 mg (1.39 mmol, Yield 94%) of the title compound.

$^1$H NMR (CDCl$_3$, ppm); δ8.19 (1H, s), 8.00–7.98 (2H, m), 7.48–7.24 (1H, m), 6.99 (1H, d), 5.24 (2H, s), 5.07 (2H, s), 3.86 (2H, t), 3.39 (2H, t), 2.60 (2H, quin), 1.40 (9H, s)

FAB MS (m/e)=703[M$^+$+1]

Preparation 86

Synthesis of t-butyl 3-(benzyloxy)-2-[4-(benzyloxy)-3-chlorophenyl]-8-(1,1-dioxo-1λ$^6$-isothiazolidin-2-yl)-4-oxo-4H-chromen-6yl(methyl)carbamate The compound prepared in Preparation 85 (900 mg, 1.28 mmol) was dissolved in tetrahydrofuran (80 ml), sodium hydride (102 mg, 60%, 2.56 mmol) and iodomethane (3 ml, 48.2 mmol) were added thereto, and the resulting mixture was stirred for 1 hour at room temperature. After completion of reaction, methanol (10 ml) was added and the resulting mixture was concentrated. To the residue was added water (50 ml), which was then stirred, filtered, and dried to give 870 mg (1.21 mmol, Yield 95%) of the title compound.

$^1$H NMR (CDCl$_3$, ppm); δ8.15 (1H, s), 8.02–7.99 (2H, m), 7.49–7.24 (1H, m), 7.00 (1H, d), 5.24 (2H, s), 5.08 (2H, s), 3.85 (2H, t), 3.40 (2H, t), 3.34 (3H, s), 2.60 (2H, quin), 1.40 (9H, s)

FAB MS (m/e)=717[M$^+$+1]

Preparation 87

Synthesis of t-butyl 2-(3-chloro-4-hydroxyphenyl)-8-(1,1-dioxo-1λ$^6$-isothiazolidin-2-yl)-3-hydroxy-4-oxo-4H-chromen-6yl(methyl)carbamate The compound prepared in Preparation 86 (800 mg, 1.11 mmol) was dissolved in 10% methanol/dichloromethane solution (50 ml), 10% palladium/carbon (50 ml) was added thereto, and hydrogenation reaction was carried out under atmospheric pressure. After completion of reaction, palladium/carbon was filtered out and the filtrate was concentrated. To the residue was added dichloromethane (50 ml), which was then stirred and filtered to give 420 mg (0.782 mmol, Yield 70%) of the title compound.

$^1$H NMR (DMSO-D$_6$, ppm); δ8.30 (1H, s), 8.07 (1H, d), 7.88 (1H, s), 7.81 (1H, s), 7.08 (1H, s), 3.89 (2H, t), 3.50 (2H, t), 3.16 (3H, s), 2.54 (2H, quin), 1.42 (9H, s)

FAB MS (m/e)=537[M$^+$+1]

EXAMPLE 25

Synthesis of 2-[6-amino-3-hydroxy-2-(4-hydroxyphenyl)-4-oxo-4H-chromen-8-yl]-1λ$^6$-isothiazolidin-1,1-dione (Compound 25)

The compound prepared in Preparation 68 (3.0 g, 5.28 mmol) was dissolved in methanol (200 ml) and dichloromethane (100 m), 10% palladium/carbon (200 mg) was added thereto, and hydrogenation reaction was carried out using a balloon. After stirring for 2 hours to complete the reaction, palladium/carbon was filtered out, and the filtrate was concentrated. To the residue was added dichloromethane (50 ml), which was then stirred and filtered to give 1.85 g (4.76 mmol, Yield 90%) of the title compound.

$^1$H NMR (DMSO-D$_6$, ppm); δ10.05 (1H, s), 9.11 (1H, s), 8.06 (2H, d), 7.18 (1H, s), 6.94 (1H, s), 6.90 (2H, s), 6.12 (2H, s), 3.84 (2H, t), 3.49 (2H, t), 2.51 (2H, quin)

FAB MS (m/e)=389[M$^+$+1]

EXAMPLE 26

Synthesis of 2-[6-(dimethylamino)-3-hydroxy-2-(4-hydroxyphenyl)-4oxo-4H-chromen-8-yl]-1λ$^6$-isothiazolidin-1,1-dione (Compound 26)

The compound prepared in Preparation 68 (200 mg, 0.352 mmol) was dissolved in methanol (30 ml) and dichloromethane (30 ml), formalin (1.0 ml, 13.3 mmol) and 10% palladium/carbon (30 ml) were added thereto, and hydrogenation reaction was carried out using a balloon. After stirring for 2 hours to complete the reaction, palladium/carbon was filtered out, and the filtrate was concentrated. To the residue was added dichloromethane (30 ml), which was then stirred and filtered to give 102 mg (0.244 mmol, Yield 70%) of the title compound.

$^1$H NMR (DMSO-D$_6$, ppm); 10.07 (1H, s), 9.18 (1H, s), 8.10 (2H, d), 7.30 (1H, s), 7.09 (1H, s), 7.92 (2H, d), 3.89 (2H, t), 3.50 (2H, t), 3.00 (6H, s), 2.50 (2H, quin)

FAB MS (m/e)=417[M$^+$+1]

EXAMPLE 27

Synthesis of 2-[6-(diethylamino)-3-hydroxy-2-(4-hydroxyphenyl)-4-oxo-4H-chromen-8-yl]-1λ$^6$-isothiazolidin-1,1-dione (Compound 27)

The compound prepared in Preparation 68 (100 mg, 0.176 mmol) was dissolved in ethanol (20 ml) and dichloromethane (20 ml), acetaldehyde (0.51 a, 8.94 mmol) and 10% palladium/carbon (20 ml) were added thereto, and hydrogenation reaction was carried out using a balloon. After stirring for 3 hours to complete the reaction, palladium/carbon was filtered out, and the filtrate was concentrated. To the residue was added dichloromethane (20 ml), which was then stirred and filtered to give 51 mg (0.115 mmol, Yield 65%) of the title compound.

$^1$H NMR (DMSO-D$_6$, ppm); δ8.00 (2H, d), 7.45 (1H, s), 7.19 (1H, s), 7.04 (2H, d), 3.86 (2H, t), 3.43 (4H, q), 3.37 (2H, t), 2.56 (2H, quin), 1.20 (6H, t)

FAB MS (m/e)445[M$^+$+1]

EXAMPLE 28

Synthesis of 2-[6-(benzylamino)-3-hydroxy-2-(4-hydroxyphenyl-4-oxo-4H-chromen-8yl]-1λ$^6$-isothiazolidin-1,1-dione (Compound 28)

The compound prepared in Preparation 68 (150 mg, 0.264 mmol) was dissolved in methanol (30 mg) and dichloromethane (30 ml), benzaldehyde (1.0 ml, 9.83 mmol) and 10% palladium/carbon (30 mg) were added thereto, and hydrogenation reaction was carried out using a balloon. After stirring for 2 hours to complete the reaction, palladium/carbon was filtered out and the filtrate was concentrated. To the residue was added dichloromethane (30 ml), which was then stirred and filtered to give 84 mg (0.175 mmol, Yield 66%) of the title compound.

$^1$H NMR (DMSO-D$_6$, ppm); δ10.08 (1H, s), 9.05 (1H, s), 8.05 (2H, d), 7.40–7.15 (6H, m), 6.93 (1H, s), 6.90 (2H, d), 6.77 (1H, t), 4.35 (2H, d), 3.83 (2H, t), 3.42 (2H, t), 2.62 (2H, quin)

FAB MS (m/e)=479[M$^+$+1]

EXAMPLE 29

Synthesis of 2-[3-hydroxy-2-(4-hydroxyphenyl)-4-oxo-6-(4-piperidinylamino)-4H-chromen-8-yl]-1λ$^6$-isothiazolidin-1,1-dione (Compound 29)

The compound prepared in Preparation 68 (350 mg, 0.615 mmol) was dissolved in methanol (50 ml) and dichloromethane (50 ml), 1-t-butoxy-4-piperidone (500 mg, 2.5 mmol), acetic acid (0.1 ml) and 10% palladium/carbon (20 mg) were added thereto, and hydrogenation reaction was carried out using a balloon. After stirring for 4 hours to complete the reaction, palladium/carbon was filtered out, and the filtrate was concentrated. To the residue were added dichloromethane (20 ml) and trifluoroacetic acid (10 ml), which was then stirred for 1 hour at room temperature. After completion of reaction, diethylether (30 ml) was added, stirred, filtered, washed with dichloromethane (20 ml), and dried to give 121 mg (0.256 mmol, Yield 42%) of the title compound.

$^1$H NMR (DMSO-D$_6$, ppm); δ8.05 (2H, d), 7.19 (1H, s), 6.96 (1H, s), 6.90 (2H, d), 6.08 (1H, d), 3.83(2H, t), 3.48 (2H, t), 3.36–3.31 (3H, m), 2.98 (2H, q), 2.62 (2H, quin), 1.90 (2H, q), 1.29 (2H, q)

FAB MS (m/e)=472[M$^+$+1]

EXAMPLE 30

Synthesis of 2-[6(cyclohexylamino)-3-hydroxy-2-(4-hydroxyphenyl)-4-oxo-4H-chromen-8-yl]-1λ$^6$-isothiazolidin-1,1-dione (Compound 30)

The compound prepared in Preparation 68 (200 mg, 0.352 mmol) was dissolved in methanol (30 ml) and dichloromethane (30 ml), cyclohexanone (1.0 ml, 9.65 mmol), acetic acid (0.1 ml) and 10% palladium/carbon (30 mg) were added thereto, and hydrogenation reaction was carried out using a balloon. After stirring for 7 hours to complete the reaction, palladium/carbon was filtered out, and the filtrate was concentrated. The residue was purified by column chromatography (eluent: methanol/dichloromethane=9/1, v/v) to give 77 mg (0.163 mmol, Yield 46%) of the title compound.

$^1$H NMR (DMSO-D$_6$, ppm); δ10.07 (1H, s), 9.09 (1H, s), 8.05 (2H, d), 7.18 (1H, s), 6.94–6.90 (3H, m), 6.04 (1H, d), 3.85 (2H, t), 3.48 (2H, t), 3.32 (1H, quin), 2.52 (2H, quin), 1.97 (2H, q), 1.75 (2H, q), 1.38–1.18 (6H, m)

FAB MS (m/e)=471[M$^+$+1]

EXAMPLE 31

Synthesis of 2-[6-anilino-3-hydroxy-2-(4-hydroxyphenyl)-4-oxo-4H-chromen-8-yl]-1λ$^6$-isothiazolidin-1,1-dione (Compound 31)

The compound prepared in Preparation 69 (70 mg, 0.108 mmol) was dissolved in methanol (10 ml) and dichloromethane (10 ml), 10% palladium/carbon (15 mg) was added thereto, and hydrogenation reaction was carried out using a balloon. After stirring for 2 hours to complete the reaction, palladium/carbon was filtered out, and the filtrate was concentrated. To the residue was added dichloromethane (20 ml), which was then stirred and filtered to give 43 mg (0.093 mmol, Yield 86%) of the title compound.

$^1$H NMR (DMSO-D$_6$, ppm); δ8.06 (1H, s), 7.78 (2H, d), 7.25–7.02 (5H, m), 6.82–6.80 (3H, m), 3.82 (2H, t), 3.51 (2H, t), 2.50 (2H, quin)

FAB MS (m/e)=465[M$^+$+1]

EXAMPLE 32

Synthesis of 2-[3-hydroxy-2-(4-hydroxyphenyl)-6-(methylamino)-4-oxo-4H-chromen-8-yl]-1λ$^6$-isothiazolidin-1,1-dione (Compound 32)

The compound prepared in Preparation 73 (85 mg, 0.146 mmol) was dissolved in methanol (15 ml) and dichloromethane (15 ml), 10% palladium/carbon (20 mg) was added thereto, and hydrogenation reaction was carried out using a balloon. After stirring for 2 hours to complete the reaction, palladium/carbon was filtered out, and the filtrate was concentrated. To the residue was added dichloromethane (20 ml), which was then stirred and filtered to give 48 mg (0.119 mmol, Yield 82%) of the title compound.

$^1$H NMR (DMSO-D$_6$, ppm); δ10.02 (1H, s), 9.20 (1H, s), 8.12 (2H, d), 7.31 (1H, s), 7.07 (1H, s), 7.91 (2H, d), 6.18 (1H, q), 3.88 (2H, t), 3.51 (2H, t), 3.00 (3H, s), 2.50 (2H, quin)

FAB MS (m/e)=403[M$^+$+1]

EXAMPLE 33

Synthesis of 2-{3-hydroxy-6-[(2-hydroxyethyl)(methyl)amino]-2-(4-hydroxyphenyl)-4-oxo-4H-chromen-8-yl}-1λ$^6$-isothiazolidin-1,1-dione (Compound 33)

The compound prepared in Preparation 74 (50 mg, 0.071 mmol) was dissolved in methanol (10 ml) and dichloromethane (10 ml), formalin (0.5 ml) and 10% palladium/carbon (10 mg) were added thereto, and hydrogenation reaction was carried out using a balloon. After stirring for 2 hours to complete the reaction, palladium/carbon was filtered out, and the filtrate was concentrated. To the residue was added dichloromethane (20 ml), which was then stirred and filtered to give 21 mg (0.0470 mmol, Yield 66%) of the title compound.

$^1$H NMR (CD$_3$OD, ppm); δ8.18 (2H, d), 7.38 (1H, s), 7.26 (1H, s), 6.91 (2H, d), 3.92 (2H, t), 3.76 (2H, t), 3.55 (2H, t), 3.47 (2H, t), 3.08 (3H, s), 2.63 (2H, quin)

FAB MS (m/e)=447[M$^+$+1]

EXAMPLE 34

Synthesis of N-[2-3-chloro-4-hydroxyphenyl)-8-(1,1-dioxo-1λ6-isothiazolidin-2-yl)-3-hydroxy-4-oxo-4H-chromen-6-yl]acetamide (Compound 34)

The compound prepared in Preparation 81 (100 mg, 0.155 mmol) was dissolved in methanol (4 ml) and dichloromethane (36 ml), 10% palladium/carbon (30 mg) was added thereto, and hydrogenation reaction was carried out using a balloon. After stirring for 2 hours to complete the reaction, palladium/carbon was filtered out, and the filtrate was concentrated. To the residue was added dichloromethane (30 ml), which was then stirred and filtered to give 58 mg (0.124 mmol, Yield 80%) of the title compound.

$^1$H NMR (DMSO-D$_6$, ppm); δ11.03 (1H, s), 10.59 (1H, s), 10.07 (1H, s), 8.23 (1H, s), 7.99 (1H, d), 7.20 (1H, s), 7.05 (1H, d), 6.92 (1H, s), 3.82 (2H, t), 3.39 (2H, t), 2.43 (2H, quin), 2.12 (3H, s)

FAB MS (m/e)=465[M$^+$+1]

EXAMPLE 35

Synthesis of 2-[6-amino-2-(3-chloro-4-hydroxyphenyl)-3-hydroxy-4-oxo-4H-chromen-8-yl]-1λ$^6$-isothiazolidin-1,1-dione (Compound 35 )

The compound prepared in Preparation 82 (100 mg, 0.166 mmol) was dissolved in methanol (4 ml) and dichloromethane (36 ml), 10% palladium/carbon (30 mg) was added thereto, and hydrogenation reaction was carried out using a balloon. After stirring for 2 hours to complete the reaction, palladium/carbon was filtered out, and the filtrate was concentrated. To the residue was added dichloromethane (30 ml), which was then stirred and filtered to give 62 mg (0.146 mmol, Yield 88%) of the title compound.

$^1$H NMR (DMSO-D$_6$, ppm); δ10.90 (1H, s), 9.37 (1H, s), 8.23 (1H, s), 8.05 (1H, d), 7.14–7.11 (3H, m), 5.60 (2H, s), 3.81 (2H, t), 3.48 (2H, t), 2.49 (2H, quin)

FAB MS (m/e)=423[M$^+$+1]

EXAMPLE 36

Synthesis of 2-[2-(3-chloro-4-hydroxyphenyl)-6-(dimethylamino)-3-hydroxy-4oxo-4H-chromen-8-yl]-1λ$^6$-isothiazolidin-1,1-dione (Compound 36)

The compound prepared in Preparation 83 (450 mg, 0.713 mmol) was dissolved in methanol (10 ml) and dichloromethane (90 ml), 10% palladium/carbon (60 mg) was added thereto, and hydrogenation reaction was carried out using a balloon. After stirring for 2 hours to complete the reaction, palladium/carbon was filtered out, and the filtrate was concentrated. To the residue was added dichloromethane (80 ml), which was then stirred and filtered to give 285 mg (0.632 mmol, Yield 89%) of the title compound.

$^1$H NMR (CD$_3$OD, ppm); δ8.33 (1H, s), 8.13 (1H, d), 7.38 (1H, s), 7.27 (1H, s), 7.01 (1H, d), 3.92 (2H, t), 3.64 (2H, t), 3.05 (6H, s), 2.65 (2H, quin)

FAB MS (m/e)=451[M$^+$+1]

EXAMPLE 37

Synthesis of 2-[2-(3-chloro-4-hydroxyphenyl)-6-(methylamino)-3-hydroxy-4-oxo-41H-chromen-8-yl]-1λ$^6$-isothiazolidin-1,1-dione (Compound 37)

The compound prepared in Preparation 87 (410 mg, 0.764 mmol) was dissolved in dichloromethane (15 ml) and trifluoroacetic acid (10 ml) and the resulting mixture was stirred for 2 hours at room temperature. After completion of reaction, the reaction solution was concentrated. To the residue was added diethylether (30 ml), which was then stirred, filtered, washed with dichloromethane (30 ml), and dried to give 323 mg (0.739 mmol, Yield 97%) of the title compound.

$^1$H NMR (DMSO-D$_6$, ppm); 8.20 (1H, s), 7.99 (1H, d), 7.16 (1H, s), 7.02 (1H, d), 6.90 (1H, s), 6.20 (1H, q), 3.90 (2H, t), 3.38 (2H, t), 2.99 (3H, d), 2.52 (2H, quin)

FAB MS (m/e)=437[M$^+$+1]

Preparation 88

Synthesis of (E)-1-(3-bromo-2-hydroxy-5-methylphenyl)-3-(3-chloro-4-methoxyphenyl)-2-propen-1-one 1-(3-Bromo-2-hydroxy-5-methylphenyl)-1-ethanone (10 g, 43.7 mmol) and 3-chloro-4-methoxybenzaldehyde (9.0 g, 1.2 molar eq.) were introduced into 80% aqueous ethanol solution (150 ml), sodium hydroxide (NaOH; 5.2 g, 3.0 molar eq.) was added thereto, and the resulting mixture was stirred for 17 hours at room temperature. After completion of reaction, the reaction solution was neutralized by 2N aqueous hydrochloric acid solution and diluted with water (150 ml). The yellow solid thus precipitated was washed with water and methanol to give 14.2 g (Yield 85%) of the purified title compound.

$^1$H NMR (CDCl$_3$, ppm) 7.88 (1H, d), 7.78 (1H, s), 7.68 (1H, s), 7.63 (1H, s), 7.54 (2H, m), 6.87 (1H, d), 3.98 (3H, s), 2.37 (3H, s).

Mass (m/e)=381[M$^+$+1]$^+$

Preparation 89

Synthesis of 8-bromo-2-(3-chloro-4-methoxyphenyl)-3-hydroxy-6-methyl-4H-chromen-4-one The compound prepared in Preparation 88 (14.2 g, 37.2 mmol) was added to methanol (200 ml), and then 2M aqueous sodium hydroxide solution (55.8 ml, 3 eq.) and 34% aqueous hydrogen peroxide (12.6 ml, 3 eq.) were added thereto After stirring for 3 hours at room temperature, the reaction solution was neutralized by 2M aqueous hydrochloric acid solution, diluted with water (200 ml), and filtered. The solid thus obtained was washed with water and methanol to give 9.17 g (Yield 65.7%) of the purified title compound.

$^1$H NMR (CDCl$_3$, ppm): 8.43 (1H, s), 8.30 (1H, d), 7.96 (1H, s), 7.77 (1H, s), 7.10 (1H, d), 6.96 (1H, br s), 3.99 (3H, s), 2.46 (3H, s).

Mass (m/e)=395[M$^+$+1]

Preparation 90

Synthesis of 8-bromo-2-(3-chloro-4-methoxyphenyl)-3-methoxy-6-methyl-4H-chromen-4-one The compound prepared in Preparation 89 (9.17 g, 24.4 mmol) was heated under reflux together with iodomethane (5.2 g, 1.5 eq.) and potassium carbonate (4.4 g, 1.3 molar eq.) in acetone (100 ml) for 5 hours. After completion of reaction, the reaction solution was cooled to room temperature and then filtered. The solid thus obtained was washed with water and acetone to give 8.0 g (Yield 79.8%) of the purified title compound.

$^1$H NMR (CDCl$_3$, ppm) 8.33 (1H, s), 8.22 (1H, d), 7.97 (1H, s), 7.73 (1H, s), 7.08 (1H, d), 3.99 (3H, s), 3.92 (3H, s).

Mass (m/e)=409[M$^+$+1]$^+$

Preparation 91

Synthesis of 2-(3-chloro-4-methoxyphenyl)-3-methoxy-6-methyl-8-(4-pyridinyl)-4H-chromen-4-one The compound prepared in Preparation 90 (3.0 g, 7.32 mmol), 1.5 equivalent of bispinacolatodiboron (2.8 g), 5 mol % of dichlorobistriphenylphosphinepalladium and 3 equivalents of potassium acetate (2.15 g) were dissolved in dimethylformamide solvent (20 ml), and the resulting mixture was reacted under nitrogen gas for 2 hours at 80° C. After the reaction solution was cooled to room temperature, 2 equivalents of 4-bromopyridine hydrochloride, 5 mol % of dichlorobistriphenylphosphinepalladium and 2M sodium carbonate solution (18.3 ml, 5 eq.) were added thereto and the resulting mixture was stirred under nitrogen gas for 15 hours at 80° C. The reaction solution was filtered and washed with dimethylformamide and 10% methanol/methylene chloride. The filtrate was concentrated and the residue was treated with water (30 ml). The pale yellow solid thus obtained was filtered, washed with water and acetone, and dried to give 2.1 g (Yield 70%) of the title compound.

$^1$H NMR (CDCl$_3$, ppm): 8.78 (2H, d), 8.12 (1H, s), 8.06 (1H, s), 7.91 (1H, d), 7.55 (3H, m), 6.97 (1H, d), 3.96 (3H, s), 3.94 (3H, s), 2.52 (3H, s).

Mass (m/e)=408 [M$^+$+1]

Preparation 92

Synthesis of 4-[2-(3-chloro-4-methoxyphenyl)-3-methoxy-6-methyl-4-oxo-4H-chromen-8-yl]-1-methylpyridinium iodide The compound prepared in Preparation 91 (2.1 g, 51.5 mmol) was refluxed together with 2 equivalents of iodomethane in acetonitrile solvent (30 ml) for 3 hours. The reaction solution was concentrated. To the residue was added methanol, which was then stirred, filtered, and washed with methanol to give 2.44 g (Yield 86%) of the title compound.

$^1$H NMR (DMSO-d$_6$, ppm): 9.15 (2H, d), 8.57 (2H, d), 8.13 (1H, s), 7.97 (2H, m), 7.88 (1H, d), 7.31 (1H, d), 4.41 (3H, s), 3.95 (3H, s), 3.85 (3H, s), 2.54 (3H, s).

Mass (m/e)=423[M$^+$+1]$^{30}$

Preparation 93
Synthesis of 2-(3-chloro-4-methoxyphenyl)-3-methoxy-6-methyl-8-(1-methyl-4-piperidinyl)-4H-chromen-4-one The compound prepared in Preparation 92 (2.44 g, 4.43 mmol) was reacted under 1 atm of hydrogen in 5 mol % $Pt_2O$, 50% methanol/dichloromethane solvent for 48 hours. The reaction mixture was filtered through a cellite pad and concentrated to give 2.3 g (Yield 93%) of the title compound in the form of hydriodate.

$^1$H NMR (CDCl$_3$, ppm): 8.09 (1H, d), 7.95 (2H, s), 7.44 (1H, s), 7.10 (1H, d), 4.00 (3H, s), 3.93 (3H, s), 3.77 (2H, m), 3.57 (1H, m), 3.03 (2H, m), 2.85 (3H, s), 2.74 (2H, m), 2.46 (3H, s), 2.23 (2H, m).

Mass (m/e)=428[M$^+$+1]$^+$

EXAMPLE 38
Synthesis of 2-(3-chloro-4-hydroxyphenyl)-3-hydroxy-6-methyl-8-(1-methyl-4-piperidinyl)-4H-chromen-4-one (Compound 38)

The compound prepared in Preparation 93 (2.3 g, 4.13 mmol) was dissolved in dichloromethane (50 ml), 5 equivalents of borontribromide was added thereto, and the resulting mixture was reacted for 10 hours at room temperature. The remaining borontribromide was decomposed by methanol and concentrated under reduced pressure. The solid thus obtained was washed with 10% methanol/dichloromethane to give 1.93 g (Yield 97%) of the title compound in the form of hydrobromide having a yellow color.

$^1$H NMR (DMSO-d$_6$, ppm): 9.60 (1H, br s), 8.23 (1H, s), 8.01 (1H, d), 7.77 (1H, s), 7.47 (1H, s), 7.19 (1H, d), 5.75 (1H, s), 3.61–3.42 (5H, m), 2.87 (3H, s), 2.44 (3H, s), 2.05 (2H, m), 1.90 (2H, m).

Mass (m/e)=400[M$^+$+1]$^+$

EXAMPLE 39
Synthesis of 2-(3-chloro-4-hydroxyphenyl)-3-hydroxy-6-methyl-8-(4-pyridinyl)-4H-chromen-4-one (Compound 39)

The compound prepared in Preparation 91 (145 mg, 0.357 mmol) was reacted according to the same procedure as Example 38 to give 156 mg (Yield 94.8%) of the title compound in the form of hydrobromide.

$^1$H NMR (CD$_3$OD, ppm): 10.90 (1H, br s), 9.80 (1H, br s), 8.99 (2H, s), 8.20 (2H, s), 8.07 (1H, s), 8.02 (1H, s), 7.84 (2H, m), 7.09 (1H, d), 2.49 (3H, s).

Mass (m/e)=380[M$^+$+1]$^+$

EXAMPLE 40
Synthesis of 4-[2-(3-chloro-4-hydroxyphenyl)-3-hydroxy-6-methyl-4-oxo-4H-chromen-8-yl]-1-methylpyridinium bromide (Compound 40).

The compound prepared in Preparation 92 (30 mg, 0.054 mmol) was reacted according to the same procedure as Example 38 to give 15 mg (Yield 58%) of the title compound in the form of hydrobromide.

$^1$H NMR (DMSO-d$_6$, ppm): 10.94 (1H, s), 9.82 (1H, s), 9.17 (2H, d), 8.56 (2H, d), 8.12 (2H, d), 7.92 (1H, s), 7.75 (1H, d), 7.10 (1H, d), 4.42 (3H, s), 2.53 (3H, s).

Mass (m/e)=394[M$^+$]

Preparation 94
Synthesis of 2-(4-methoxyphenyl)-3-methoxy-6-methyl-8-(4-pyridinyl)-4H-chromen-4-one 1-(3-Bromo-2-hydroxy-5-methylphenyl)-1-ethanone (500 mg, 2.18 mmol) and 4-methoxybenzaldehyde (0.36 g, 1.2 molar eq.) were reacted according to the same procedure as Preparations 88, 89, 90 and 91 to give 417 mg (Total Yield 51%) of the title compound.

$^1$H NMR (CDCl$_3$, ppm): 8.74 (2H, d), 8.12 (1H, s), 7.92 (2H, d), 7.57 (2H, d), 7.50 (1H, s), 6.94 (2H, d), 3.88 (3H, s), 3.85 (3H, s), 2.50 (3H, s)

Mass (m/e)=374[M$^+$+1]$^+$

Preparation 95
Synthesis of 2-(4-methoxyphenyl)-3-methoxy-6-methyl-8-(1-methyl-4-piperidinyl)-4H-chromen-4-one The compound prepared in Preparation 94 (100 mg, 0.268 mmol) was reacted according to the same procedure as Preparations 92 and 93 to give 108 mg (Total Yield 85%) of the title compound in the form of hydriodate.

$^1$H NMR (DMSO-d$_6$, ppm): 8.16 (2H, d), 7.86 (1H, s), 7.49 (1H, s), 6.97 (2H, d), 3.90 (3H, s), 3.89 (3H, s), 3.60 (3H, m), 2.91 (5H, m), 2.52 (3H, s), 2.22–2.20 (4H, m).

Mass (m/e)=394 [M$^+$+1]$^+$

EXAMPLE 41
Synthesis of 2-(4-hydroxyphenyl)-3-hydroxy-6-methyl-8-(1-methyl-4-piperidinyl)-4H-chromen-4-one (Compound 41)

The compound prepared in Preparation 95 (50 mg, 0.095 mmol) was reacted according to the same procedure as Example 38 to give 35 mg (Yield 82%) of the title compound in the form of hydrobromide.

$^1$H NMR (CD$_3$OD, ppm): 8.16 (2H, d), 7.86 (1H, s), 7.49(1H, s), 6.97 (2H, d), 3.67 (3H, m), 3.35 (2H, m), 2.91 (3H, s), 2.47 (3H, s), 2.26 (2H, m), 2.07 (2H, m).

Mass (m/e)=366 [M$^+$+1]$^+$

Preparation 96
Synthesis of 2-(3-methyl-4-methoxyphenyl)-3methoxy-6-methyl-8-(4-pyridinyl)-4H-chromen-4-one 1-(3-Bromo-2-hydroxy-5-methylphenyl)-1-ethanone (500 mg, 2.18 mmol) and 3-methyl-4-methoxybenzaldehyde (0.4 g, 1.2 molar eq.) were reacted according to the same procedure as Preparations 88, 89, 90 and 91 to give 252 mg (Total Yield 30%) of the title compound.

$^1$H NMR (CDCl$_3$, ppm): 8.76 (2H, d), 8.13 (1H, s), 7.90 (1H, d), 7.76 (1H, s), 7.56 (2H, d), 7.52 (1H, s), 6.87 (1H, d), 3.90 (3H, s), 3.89 (3H, s), 2.52 (3H, s)

Mass (m/e)=388[M$^+$+1]$^+$

Preparation 97
Synthesis of 2-(3-methyl-4-methoxyphenyl)-3-methoxy-6-methyl-8-(1-methyl-4-piperidinyl)-4H-chromen-4-one The compound prepared in Preparation 96 (252 mg, 0.65 mmol) was reacted according to the same procedure as Preparations 92 and 93 to give 178 mg (Total Yield 51%) of the title compound in the form of hydriodate.

1H NMR (CDCl$_3$+CD$_3$OD, ppm): 7.90 (1H, s), 7.86 (1H, d), 7.77 (1H, s), 7.40 (1H, s), 6.96 (1H, d), 3.89 (3H, s), 3.80 (3H, s), 3.64 (2H, m), 3.50 (1H, m), 2.91 (2H, m), 2.76 (3H, s), 2.42 (3H, s), 2.26 (3H, s), 2.22–2.20 (4H, m).

Mass (m/e)=408 [M$^+$+1]$^+$

EXAMPLE 42
Synthesis of 3-hydroxy-2-(4-hydroxy-3-methylphenyl)-6-methyl-8-(1-methyl-4-piperidinyl)-4H-chromen-4-one (Compound 42)

The compound prepared in Preparation 97 (178 g, 0.332 mmol) was reacted according to the same procedure as Example 38 to give 115 mg (Yield 75%) of the title compound in the form of hydrobromide.

$^1$H NMR (CD$_3$OD, ppm): 8.02 (1H, s), 7.96 (1H, d), 7.85 (1H, s), 7.50 (1H, s), 6.92 (1H, d), 3.69 (3H, m), 3.44 (2H, m), 2.98 (3H, s), 2.48 (3H, s), 2.30 (5H, m), 2.10 (2H, m).

Mass (m/e)=380[M$^+$+1]$^+$

Preparation 98
Synthesis of 2-(3-trifluoromethyl-4-methoxyphenyl)-3-methoxy-6-methyl-8-(4-pyridinyl)-4H-chromen-4one 1-(3-Bromo-2-hydroxy-5-methylphenyl)-1-ethanone (500 mg, 2.18 mmol) and 3-trifluoromethyl-4-methoxybenzaldehyde (0.4 g, 1.2 molar eq.) were reacted according to the same procedure as Preparations 88, 89, 90, and 91 to give 252 mg (Total Yield 30%) of the title compound.

$^1$H NMR (CDCl$_3$, ppm): 8.75 (2H, d), 8.20 (2H, m), 8.10 (1H, s), 7.50 (4H, m), 7.05 (1H, d), 3.95 (3H, s), 3.92 (3H, s), 2.51 (3H, s).

Mass (m/e)=442[M$^+$+1]$^+$

Preparation 99

Synthesis of 2-(3-trifluoromethyl-4-methoxyphenyl)-3-methoxy-6-methyl-8-(1-methyl-4-piperidinyl)-4H-chromen-4-one The compound prepared in Preparation 98(100 mg, 0.226 mmol) was reacted according to the same procedure as Preparations 92 and 93 to give 100 mg (Total Yield 75%) of the title compound in the form of hydriodate.

$^1$H NMR (DMSO-d$_6$, ppm): 8.64 (1H, s), 8.25 (1H, s), 7.81 (1H, s), 7.45 (1H, s), 7.22 (1H, d), 4.00 (3H, s), 3.96 (3H, s), 3.65–3.30 (5H, m), 2.89 (3H, s), 2.46 (3H, s), 2.21 (2H, m), 1.94 (2H, m).

Mass (m/e)=462[M$^+$+1]$^+$

EXAMPLE 43

Synthesis of 3-hydroxy-2-(4-hydroxy-3-trifluoromethylphenyl)-6-methyl-8-(1-methyl-4-piperidinyl)-4H-chromen-4-one (Compound 43)

The compound prepared in Preparation 99 (100 mg, 0.169 mmol) was reacted according to the same procedure as Example 38 to give 69 mg (Yield 79%) of the title compound in the form of hydrobromide.

$^1$H NMR (DMSO-d$_6$, ppm): 9.60 (1H, br s), 9.39 (1H, s), 8.66 (1H, s), 8.30 (1H, d), 7.79 (1H, s), 7.46 (1H, s), 6.84 (1H, d), 4.39 (1H, m), 3.65–3.33 (4H, m), 2.92 (3H, s), 2.43 (3H, s), 2.32 (2H, m), 2.14 (2H, m).

Mass (m/e)=434[M$^+$+1]$^+$

Preparation 100

Synthesis of 4-[2-(3-chloro-4-methoxyphenyl)-3-methoxy-6-methyl-4-oxo-4H-chromen-5-yl]-1-(2-methoxyethyl)pyridinium bromide The compound prepared in Preparation 91 (50 mg, 0.122 mmol) was refluxed with 2 equivalents of 2-bromoethyl methyl ether in acetonitrile solvent (5 ml) for 3 hours. The reaction solution was concentrated and the residue was treated with methanol, filtered, and washed with methanol to give 52 mg (Yield 78%) of the title compound.

$^1$H NMR (DMSO-d$_6$, ppm): 9.15 (2H, d), 8.57 (2H, d), 8.13 (1H, s), 7.97 (2H, m), 7.88 (1H, d), 7.31 (1H, d), 4.41 (3H, s), 3.95 (6H, d), 3.85 (3H, s), 3.80 (2H, t), 2.54 (3H, s).

Mass (m/e)=466[M$^+$]ms=545

Preparation 101

Synthesis of 2-(3-chloro-4-methoxyphenyl)-3-methoxy-8-[1-(2-methoxyethyl)-4-piperidinyl]-6-methyl-4H-chromen-4-one The compound prepared in Preparation 100 (45 mg, 0.082 mmol) was reacted according to the same procedure as Preparation 93 to give 30 mg (Yield 66%) of the title compound in the form of hydrobromide.

$^1$H NMR (CDCl$_3$, ppm): 8.09 (1H, d), 7.95 (2H, s), 7.44 (1H, s), 7.10 (1H, d), 4.00 (3H, s), 3.93 (6H, d), 3.80 (2H, t), 3.77 (4H, m), 3.57 (1H, m), 3.03 (2H, m), 2.85 (3H, s), 2.74 (2H, m), 2.46 (3H, s), 2.23 (2H, m).

Mass (m/e)=472[M$^+$+1]$^+$

EXAMPLE 44

Synthesis of 2-(3-chloro-4-hydroxyphenyl)-3-hydroxy-8-[1-(2-hydroxy-ethyl)-4-piperidinyl]-6-methyl-4H-chromen-4-one The compound prepared in Preparation 101 (25 mg, 0.045 mmol) was reacted according to the same procedure as Example 38 to give 15 mg (Yield 65%) of the title compound in the form of hydrobromide.

$^1$H NMR (DMSO-d$_6$, ppm): 9.60 (1H, br s), 8.23 (1H, s), 8.01 (1H, d), 7.77 (1H, s), 7.47 (1H, s), 7.19 (1H, d), 5.75 (1H, s), 3.61–3.42 (7H, m), 2.87 (2H, m), 2.44 (3H, s), 2.05 (2H, m), 1.90 (2H, m).

Mass (m/e)=430 [M$^+$+1]$^+$

Preparation 102

Synthesis of 4-[2-(3-chloro-4-methoxyphenyl)-3-methoxy-6-methyl-4-oxo-4H-chromen-8-yl]-1-[2-(1,3-dioxo-1,3-dihydro-2H-isoindol-2-yl)ethyl]pyridinium bromide The compound prepared in Preparation 91 (50 mg, 0.122 mmol) was reacted with 2 equivalents of N-(2-bromoethyl) phthalimide according to the same procedure as Preparation 100 to give 60 mg (Yield 74%) of the title compound.

$^1$H NMR DMSO-d$_6$, ppm): 9.15 (2H, d), 8.57 (2H, d), 8.13 (1H, s), 7.97 (2H, m), 7.88 (1H, d), 7.55–7.40 (4H, m), 7.31 (1H, d), 4.41 (2H, m), 3.95 (3H, s), 3.85 (3H, s), 2.54 (3H, s), 2.23 (2H, t).

Mass (m/e)=581[M+]ms=660

Preparation 103

Synthesis of 2-(2-{4-12-(3-chloro-4-methoxyphenyl)-3-methoxy-6-methyl-4-oxo-4H-chromen-8-yl]-1-piperidinyl}ethyl)-2H-isoindol-1,3 (2H)-dione The compound prepared in Preparation 102 (50 mg, 0.075 mmol) was reacted according to the same procedure as Preparation 93 to give 45 mg (Yield 89%) of the title compound in the form of hydrobromide.

$^1$H NMR (DMSO-d$_6$, ppm): 8.09 (1H, d), 7.95 (2H, s), 7.58–7.47 (4H, m), 7.44 (1H, s), 7.10 (1H, d)>4.00 (3H, s), 3.93 (3H, s), 3.77 (2H, m), 3.57 (1H, m), 3.03 (2H, m), 2.85 (2H, s), 2.74 (2H, m), 2.46 (3H, s), 2.23 (4H, m).

Mass (m/e)=587 [M$^+$+1]$^+$

Preparation 104

Synthesis of 2-(2-{4-[2-(3-chloro-4-hydroxyphenyl)-3-hydroxy-6-methyl-4-oxo-4H-chromen-8-yl]-1-piperidinyl}ethyl)-2H-isoindol-1,3 (2H)-dione The compound prepared in Preparation 103 (40 mg, 0.060 mmol) was reacted according to the same procedure as Example 38 to give 25 mg (Yield 65%) of the title compound in the form of hydrobromide.

$^1$H NMR (DMSO-d$_6$, ppm): 9.60 (1H, br s), 8.23 (1H, s), 8.01 (1H, d), 7.77 (1H, s), 7.62–7.49 (4H, m), 7.47 (1H, s), 7.19 (1H, d), 5.75 (1H, s), 3.61–3.42 (5H, m), 2.87 (2H, t), 2.44 (3H, s), 2.23 (2H, t), 2.05 (2H, m), 1.90 (2H, m).

Mass (m/e)=559[M$^+$+1]$^+$

EXAMPLE 45

Synthesis of 8-[1-2-aminoethyl)-4-piperidinyl]-2-(3-chloro-4-hydroxyphenyl)-3-hydroxy-6-methyl-4H-chromen-4-one (Compound 45)

The compound prepared in Preparation 104 (25 mg, 0.040 mmol) was introduced into ethanol (5 ml), 3 equivalents of hydrazine was added thereto, and the resulting mixture was heated to 60° C. for 1 hour. After the reaction solution was cooled to room temperature, aqueous sodium carbonate solution was added. The resulting solid was filtered to give 12 mg (Yield 70%) of the title compound.

$^1$H NMR (DMSO-d$_6$, ppm): 9.60 (1H, br s), 8.23 (1H, s), 8.01 (1H, d), 7.77 (1H, s), 7.47 (1H, s), 7.19 (1H, d), 5.75 (1H, s), 3.61–3.42 (5H, m), 2.87 (2H, t),2.55 (2H, t), 2.44 (3H, s), 2.05 (2H, m), 1.90 (2H, m).

Mass (m/e)=429[M$^+$+1]$^+$

Experiment 1

Inhibitory activity against CDK2 and CDK4

The inhibitory activity against CDK2 was measured by referring to Kitagawa, M. et al., *Oncogene* 9; 2549, 1994 and that against CDK4 was measured by referring to Carlson, B. A. et al., *Cancer Research* 56; 2473, 1996.

Active CDK2/cyclin A used in this experiment is a conjugate of human CDK2 protein labelled with histidine and cyclin A protein; is purified from an insect cell infected both with baculovirus expressing His-CDK2 gene and baculovirus expressing cyclin A gene; and has a unit activity of 14 nmole/min/mg and Km value against ATP of 22 μM. Active CDK4/cyclin D1 used in this experiment is a conjugate of human CDK4 protein bound to GST (glutathione-S-transferase) and cyclin D1 protein; is expressed and purified from an insect cell; and has a unit activity of 57 nmole/min/mg and Km value against ATP of 940 μM. The part of amino acid positions 780 to 928 of C-terminus of human Rb protein was isolated, N-terminus thereof was labelled with GST protein, large amount thereof was expressed in bacteria and purified to be used as the substrate for the enzyme.

The activities of CDK2/cyclin A and CDK4/cyclin D1 were determined as follows. About 100 ng of enzyme was reacted in a total 100 μl of 20 mM Tris(pH 8.0), 100 mM NaCl, 10 mM MgCl$_2$ buffer solution containing 20 μg of GST-Rb protein, 100 μM of ATP and 5 μCi of p$^{32}$-γ-ATP at 30° C. for 30 minutes. Then, EDTA was added to a concentration of 20 mM to stop the enzyme reaction. Subsequently, 30 μl of 50% glutathione bead (purchased from Pharmacia) was added to attach GST-Rb to the bead, which was washed three times with 20 mM Tris(pH 8.0), 100 mM NaCl, 10 mM EDTA solution, and then scintillation counting was carried out. To analyze the inhibitory activity of the compound, the inhibitor having a proper concentration was added to the enzyme reaction solution, and then the enzyme activity was measured according to the above method.

The inhibitory activity against CDK2 and CDK4 of the compound of formula (1) according to the present invention was represented as IC$_{50}$ value (see the following Table 1).

TABLE 1

| Compound No. | FAB MS (M + 1) | CDK2 IC$_{50}$ (μM) | CDK4 IC$_{50}$ (μM) |
|---|---|---|---|
| 1 | 299 | 1.4 | 20.0 |
| 2 | 359 | 4.5 | 7.7 |
| 3 | 371 | 6.0 | 3.9 |
| 4 | 284 | 2.1 | 2.1 |
| 6 | 326 | 30.0 | 10.0 |
| 7A | 383 | 18.0 | 47.0 |
| 7B | 341 | 3.0 | 17.0 |
| 9 | 302 | 14.0 | 16.0 |
| 10 | 385 | 30.0 | 100.0 |
| 11 | 283 | 150.0 | 50.0 |
| 12 | 284 | 2.0 | 2.1 |
| 13 | 301 | 1000.0 | 50.0 |
| 14 | 363 | 500.0 | 11.0 |
| 15 | 388 | 0.250 | 0.550 |
| 16 | 406 | 0.450 | 1.100 |
| 17 | 422 | 0.185 | 0.195 |
| 18 | 466 | 0.075 | 0.210 |
| 19 | 413 | 1.400 | 0.790 |
| 20 | 404 | 1000 | 500 |
| 21 | 424 | 13.00 | 24.00 |
| 22 | 402 | 0.700 | 2.000 |
| 23 | 418 | 1.500 | 5.000 |
| 24 | 456 | 0.250 | 2.100 |
| 25 | 389 | 0.088 | 1.2 |
| 26 | 417 | 0.22 | 0.71 |

TABLE 1-continued

| Compound No. | FAB MS (M + 1) | CDK2 IC$_{50}$ (μM) | CDK4 IC$_{50}$ (μM) |
|---|---|---|---|
| 27 | 445 | 9 | 7.1 |
| 28 | 479 | 2.24 | 3.2 |
| 29 | 472 | 1.8 | 1.7 |
| 30 | 471 | 5.6 | 1.6 |
| 31 | 465 | 1.4 | 3 |
| 32 | 403 | 0.224 | 0.54 |
| 33 | 447 | 0.6 | 0.9 |
| 34 | 465 | 1.3 | 1.8 |
| 35 | 423 | 0.07 | 0.18 |
| 36 | 451 | 0.5 | 0.6 |
| 37 | 437 | 0.2 | 0.18 |
| 38 | 400 | 0.50 | 0.12 |
| 39 | 380 | 0.13 | 0.28 |
| 40 | 394 | 0.70 | 0.31 |
| 41 | 366 | 0.56 | 0.15 |
| 42 | 380 | 0.178 | 0.65 |
| 43 | 434 | 6.3 | <1 |
| 44 | 430 | <1 | <1 |
| 45 | 429 | <1 | <1 |

Experiment 2

Acute Toxicity Test

To determine the acute oral toxicities of the test compounds, solutions containing a compound in different concentrations from each other were administered orally to ICR male with a dose of 10 ml/kg body weight. After oral administration, lethality and symptoms for 7 days were observed, and LD$_{50}$ (mg/kg) was calculated according to Litchfield-Wilcoxon method. The results are represented in the following Table 2.

TABLE 2

| Test Compound | LD$_{50}$ (mg/kg) |
|---|---|
| Example 15 | >3,000 |
| Example 17 | >3,000 |
| Example 36 | >3,000 |
| Example 37 | >3,000 |
| Example 38 | >3,000 |
| Example 40 | >3,000 |

What is claimed is:

1. A compound represented by the following formula (1):

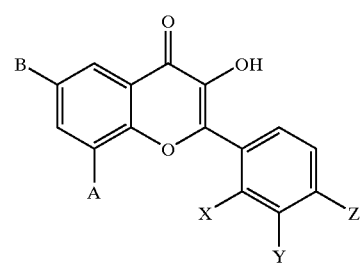

in which

A represents a structure selected from a group consisting of

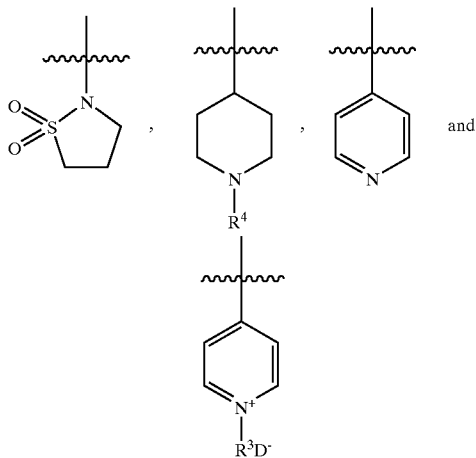

wherein $R^4$ represents hydrogen or $C_1$–$C_6$-alkyl which is optionally substituted by amino or hydroxy, $R^3$ represents $C_1$–$C_6$-alkyl which is optionally substituted by amino or hydroxy and D represents halogen, B represents methyl, or represents amino which is optionally mono-or disubstituted by substituents selected from a group consisting of $C_1$–$C_6$-alkyl, hydroxy-$C_1$–$C_6$-alkyl, $C_3$–$C_6$-cycloalkyl, acetyl, phenyl, benzyl and piperidinyl, X, Y and Z independently of one another represent hydrogen, hydroxy, nitro, cyano or halogen, or represent amino which is optionally substituted by $C_1$–$C_4$-alkyl, $C_1$–$C_4$-alkylcarbonyl or carbamoyl, or represent $C_1$–$C_4$-alkyl which is optionally substituted by hydroxy or halogen, pharmaceutically acceptable salt, hydrate, solvate or isomer thereof.

2. The compound of claim 1 selected from a group consisting of the following:

2-[3-hydroxy-2-(4-hydroxyphenyl)-6-methyl-4-oxo-4H-chromen-8-yl]-1$\lambda^6$-isothiazolidin-1,1-dione (Compound 15);

2-[2-(3-fluoro-4-hydroxyphenyl)-3-hydroxy-6-methyl-4-oxo-4H-chromen-8-yl]-1$\lambda^6$-isothiazolidin-1,1-dione (Compound 16);

2-[2-(3-chloro-4-hydroxyphenyl)-3-hydroxy-6-methyl-4-oxo-4H-chromen-8-yl]-1$\lambda^6$-isothiazolidin-1,1-dione (Compound 17);

2-[2-(3-bromo-4-hydroxyphenyl)-3-hydroxy-6-methyl-4-oxo-4H-chromen-8-yl]-1$\lambda^6$-isothiazolidin-1,1-dione (Compound 18);

5-[8-(1,1-dioxo-1$\lambda^6$-isothiazolidin-2-yl)-3-hydroxy-6-methyl-4-oxo-4H-chromen-2-yl]-2-hydroxybenzonitrile (Compound 19);

2-[2-(2,4-dihydroxyphenyl)-3-hydroxy-6-methyl-4-oxo-4H-chromen-8-yl]-1$\lambda^6$-isothiazolidin-1,1-dione (Compound 20);

2-[2-(3-chloro-4-fluorophenyl)-3-hydroxy-6-methyl-4-oxo-4H-chromen-8-yl]-1$\lambda^6$-isothiazolidin-1,1-dione (Compound 21);

2-[3-hydroxy-2-(4-hydroxy-3-methylphenyl)-6-methyl-4-oxo-4H-chromen-8-yl]-1$\lambda^6$-isothiazolidin-1,1-dione (Compound 22);

2-{3-hydroxy-2-[4-hydroxy-3-(hydroxymethyl)phenyl]-6-methyl-4-oxo-4H-chromen-8-yl}-1$\lambda^6$-isothiazolidin-1,1-dione (Compound 23);

2-[3-hydroxy-2-(4-hydroxy-3-trifluoromethylphenyl)-6-methyl-4-oxo-4H-chromen-8-yl]-1$\lambda^6$-isothiazolidin-1,1-dione (Compound 24);

2-[6-amino-3-hydroxy-2-(4-hydroxyphenyl)-4-oxo-4H-chromen-B-yl]-1$\lambda^6$-isothiazolidin-1,1-dione (Compound 25);

2-[6-(dimethylamino)-3-hydroxy-2-(4-hydroxyphenyl)-4-oxo-4H-chromen-8-yl]-1$\lambda^6$-isothiazolidin-1,1-dione (Compound 26);

2-[6-(diethylamino)-3-hydroxy-2-(4-hydroxyphenyl)-4-oxo-4H--chromen-8-yl]-1$\lambda^6$-isothiazolidin-1,1-dione (Compound 27);

2-[6-(benzylamino)-3-hydroxy-2-(4-hydroxyphenyl)-4-oxo-4H-chromen-8-yl]-1$\lambda^6$-isothiazolidin-1,1-dione (Compound 28);

2-[3-hydroxy-2-(4-hydroxyphenyl)-4-oxo-6-(4-piperidinylamino)-4H-chromen-8-yl]-1$\lambda^6$-isothiazolidin-1,1-dione (Compound 29);

2-[6-(cyclohexylamino)-3-hydroxy-2-(4-hydroxyphenyl)-4-oxo-4H-chromen-8-yl]-1$\lambda^6$-isothiazolidin-1,1-dione (Compound 30);

2-[6-anilino-3-hydroxy-2-(4-hydroxyphenyl)-4-oxo-4H-chromen-8-yl]-1$\lambda^6$-isothiazolidin-1,1-dione (Compound 31);

2-[3-hydroxy-2-(4-hydroxyphenyl)-6-(methylamino)-4-oxo-4H-chromen-8-yl]-1$\lambda^6$-isothiazolidin-1,1-dione (Compound 32);

2-{3-hydroxy-6-[(2-hydroxyethyl) (methyl)amino]-2-(4-hydroxyphenyl)-4-oxo-4H-chromen-8-yl}-1$\lambda^6$-isothiazolidin-1,1-dione (Compound 33);

N-[2-(3-chloro-4-hydroxyphenyl)-8-(1,1-dioxo-1$\lambda^6$-isothiazolidin-2-yl)-3-hydroxy-4-oxo-4H-chromen-6-yl]acetamide (Compound 34);

2-[6-amino-2-(3-chloro-4-hydroxyphenyl)-3-hydroxy-4-oxo-4H-chromen-8-yl]-1$\lambda^6$-isothiazolidin-1,1-dione (Compound 35);

2-[2-(3-chloro-4-hydroxyphenyl)-6-(dimethylamino)-3-hydroxy-4-oxo-4H-chromen-8-yl]-1$\lambda^6$-isothiazolidin-1,1-dione (Compound 36);

2-[2-(3-chloro-4-hydroxyphenyl)-6-(methylamino)-3-hydroxy-4-oxo-4H-chromen-8-yl]-1$\lambda^6$-isothiazolidin-1,1-dione (Compound 37);

2-(3-chloro-4-hydroxyphenyl)-3-hydroxy-6-methyl-8-(1-methyl-4-piperidinyl)-4H-chromen-4-one (Compound 38);

2-(3-chloro-4-hydroxyphenyl)-3-hydroxy-6-methyl-8-(4-pyridinyl)-4H-chromen-4-one (Compound 39);

4-[2-(3-chloro-4-hydroxyphenyl)-3-hydroxy-6-methyl-4-oxo-4H-chromen-8-yl]-1-methylpyridinium bromide (Compound 40);

2-(4-hydroxyphenyl)-3-hydroxy-6-methyl-8-(1-methyl-4-piperidinyl)-4H-chromen-4-one (Compound 41);

3-hydroxy-2-(4-hydroxy-3-methylphenyl)-6-methyl-8-(1-methyl-4-piperidinyl)-4H-chromen-4-one (Compound 42);

3-hydroxy-2-(4-hydroxy-3-trifluoromethylphenyl)-6-methyl-8-(1-methyl-4-piperidinyl)-4H-chromen-4-one (Compound 43);

2-(3-chloro-4-hydroxyphenyl)-3-hydroxy-8-[1-(2-hydroxyethyl)-4-piperidinyl]-6-methyl-4H-chromen-4-one (Compound 44); and 8-[1-(2-aminoethyl)-4-piperidinyl]-2-(3-chloro-4-hydroxyphenyl)-3-hydroxy-6-methyl-4H-chromen-4-one (Compound 45).

3. A process for preparing the compound of formula (1) as defined in claim 1 wherein (a) a compound represented by the following formula (5):

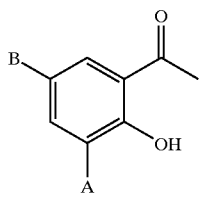
(5)

in which A and B are defined as claim 1, is reacted with an aldehyde represented by the following formula (6):

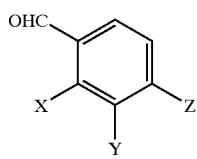
(6)

in which X, Y and Z are defined as claim 1, to produce a compound represented by the following formula (7):

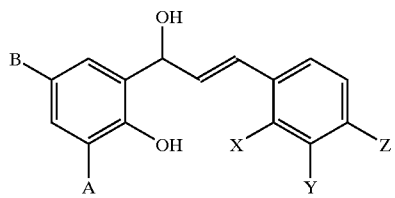
(7)

in which A, B, X, Y and Z are defined as claim 1, and the compound of formula (7) thus prepared is cyclized in the presence of a base to produce the compound of formula (1) as defined in claim 1;

(b) a compound represented by the following formula (8):

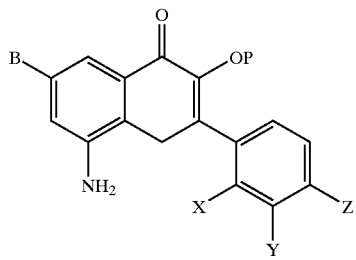
(8)

in which B, X, Y and Z are defined as claim 1 and P represents hydroxy-protecting group, is reacted with 3-chloropropanesulfonylchloride in the presence of a base and a catalyst to produce a compound represented by the following formula (9):

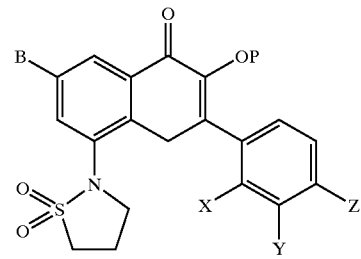
(9)

in which B, X, Y and Z are defined as claim 1 and P is defined as previously described, and the compound of formula (9) thus prepared is deprotected to produce a compound represented by the following formula (1a):

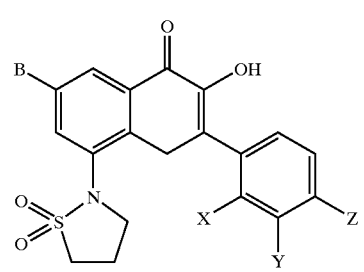
(1a)

in which B, X, Y and Z are defined as claim 1;

(c) a compound represented by the following formula (10):

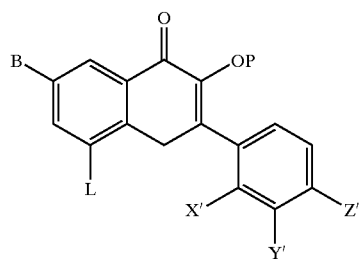
(10)

in which B is defined as claim 1 and P is defined as previously described, L represents leaving group, and X', Y' and Z' each are identical with X, Y and Z, respectively, but hydroxy group(s) is(are) protected, is reacted with 4-halogenopyridine in the presence of a base and a catalyst and then deprotected to produce a compound represented by the following formula (1b):

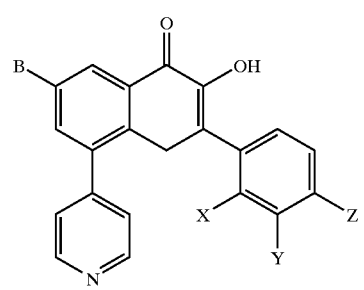
(1b)

in which B, X, Y and Z are defined as claim 1;

(d) the compound obtained before the deprotection step in process variant (c) is reacted with a compound represented by the following formula (11):

$$R^3D \quad (11)$$

in which $R^3$ and D are defined as claim 1, and then deprotected to produce a compound represented by the following formula (1c):

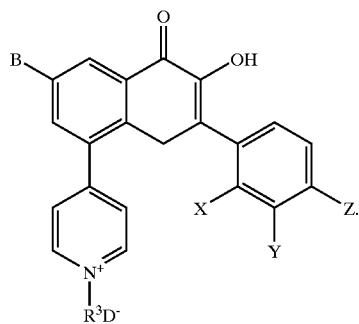

(1c)

in which B, X, Y, Z, $R^3$ and D are defined as claim 1;

(e) the compound obtained before the deprotection step in process variant (d) is reduced and deprotected to produce a compound represented by the following formula (1d):

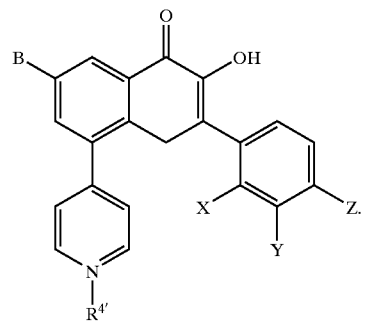

(1d)

in which B, X, Y and Z are defined as claim 1 and $R^{4'}$ is identical with $R^4$ but other than hydrogen;

and, optionally, hydrolysis, protection, deprotection, reduction or amidation reaction is further carried out.

4. A composition for suppression or treatment of cancer and diseases induced by cell proliferation which comprises the compound of formula (1), pharmaceutically acceptable salt, hydrate, solvate, or isomer thereof, as defined in claim 1, as an active component together with pharmaceutically acceptable carriers.

5. The composition of claim 4, wherein the diseases induced by cell proliferation are selected from the group consisting of inflammation, angiostenosis, and angiogenesis.

* * * * *